United States Patent [19]

Gante et al.

[11] 4,110,447
[45] Aug. 29, 1978

[54] ANTI-INFLAMMATORY (HOLO-4-BIPHENYLYL)-ALKANOLAMINES

[75] Inventors: Joachim Gante; Hans-Adolf Kurmeier; Erich Schacht; Werner Mehrhof; Dieter Orth; Albrecht Wild; Zdenek Simane, all of Darmstadt, Fed. Rep. of Germany

[73] Assignee: Merck Patent Gesellschaft mit beschraenkter Haftung, Darmstadt, Fed. Rep. of Germany

[21] Appl. No.: 624,762

[22] Filed: Oct. 22, 1975

[30] Foreign Application Priority Data

Oct. 26, 1974 [DE] Fed. Rep. of Germany ....... 2450989
May 28, 1975 [DE] Fed. Rep. of Germany ....... 2523565

[51] Int. Cl.² .................... C07D 295/08; C07C 91/06
[52] U.S. Cl. .................... 424/244; 548/335;
260/239 B; 548/341; 260/293.83; 260/293.84;
260/326 R; 260/326 A; 260/326.5 R; 260/326.5 M; 260/562 P; 260/570 R; 260/570.5 R;
260/570.6; 260/570.8 R; 424/267; 424/248.4;
424/248.57; 424/248.58; 424/250; 424/273 R;
424/274; 424/330; 542/400; 542/442; 542/455;
542/458; 542/468; 542/469; 542/470; 544/170;
544/174; 544/178; 544/237; 544/401
[58] Field of Search ........ 260/239 B, 293.84, 326.5 R, 260/570.6; 424/267, 274, 330, 244

[56] References Cited

U.S. PATENT DOCUMENTS

| 2,543,271 | 2/1951 | Bambas | 260/570.6 |
| 2,680,115 | 6/1954 | Ruddy et al. | 260/294.7 |
| 2,723,269 | 11/1955 | Denton | 260/294.7 |
| 2,771,469 | 11/1956 | Schultz | 260/570.6 |
| 3,058,987 | 10/1962 | Albrecht et al. | 260/293.84 |

OTHER PUBLICATIONS

Dawes, Brit. J. Pharmacol., 1946, vol. 1, pp. 90–111.
Lindner et al., Chem. Abst., 1959, vol. 53, cols. 11764–11765.
Nardi et al., Chem. Abst., 1966, vol. 60, col. 9271.
Sam et al., Chem. Abst., 1969, vol. 71, No. 101447x.
Work, J. Chem. Soc. (London), 1940, pp. 1315–1320.

Primary Examiner—Natalie Trousof
Attorney, Agent, or Firm—Millen & White

[57] ABSTRACT

Compounds of the formula

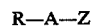

R—A—Z wherein R is 4-biphenylyl or 4-phenoxyphenyl or a corresponding group monosubstituted or polysubstituted by one or more of F, Cl and Br; A is —CH(CH$_3$)—CH$_2$—(CH$_2$)$_n$—, —C(CH$_3$)=CH—(CH$_2$)$_n$— or —C(OH) (CH$_3$)—CH$_2$—(CH$_2$)$_n$—; Z is —NR$^1$R$^2$, imidazol-1-yl, phthalimido or 4,5-dihydro-4-oxophthalazin-1-yl-amino; R$^1$ and R$^2$ each are H or alkyl, azaalkyl or acyl, each of 1 - 6 carbon atoms or, collectively, are alkylene of 4 - 7 carbon atoms, 3-oxapentamethylene or 3-R$^3$-3-azapentamethylene; R$^3$ is H or alkyl or hydroxyalkyl each of up to 6 carbon atoms; and n is 0, 1 or 2, and their physiologically acceptable acid addition salts possess anti-inflammatory, anti-arteriosclerotic and serum cholesterol and triglyceride level lowering activities.

17 Claims, No Drawings

ANTI-INFLAMMATORY (HOLO-4-BIPHENYLYL)-ALKANOLAMINES

BACKGROUND OF THE INVENTION

This invention relates to novel araliphatic nitrogen compounds.

SUMMARY OF THE INVENTION

In a composition aspect, this invention relates to compounds of the general formula I.

wherein R is a 4-biphenylyl or 4-phenoxyphenyl or a corresponding group monosubsituted or polysubstituted by one or more of F, Cl and Br; A is —CH(CH$_3$)—CH$_2$—(CH$_2$)$_n$—, —C(CH$_3$)=CH—(CH$_2$)$_n$— or —C(OH)—(CH$_3$)—CH$_2$—(CH$_2$)$_n$—, Z is —NR$^1$R$^2$, imidazol-1-yl, phthalimido or 4,5-dihydro-4-oxophthalazin-1-yl-amino; R$^1$ and R$^2$ each are H or alkyl, azaalkyl or acyl, each of 1 - 6 carbon atoms or collectively are alkylene of 4 - 7 carbon atoms, 3-oxapentamethylene or 3-R$^3$-3-azapentamethylene; R$^3$ is H or alkyl or hydroxyalkyl each of up to 6 carbon atoms; and n is 0, 1 or 2, and their physiologically acceptable acid addition salts.

In another composition aspect, this invention relates to pharmaceutical compositions, comprising, in unit dosage form, a novel compound of this invention in admixture with a pharmaceutically acceptable carrier.

In process aspects, this invention relates to processes for the production and use of the novel compounds of this invention.

DETAILED DISCUSSION

In the compounds of Formula I, R is preferably unsubstituted 4-biphenylyl or 4-phenoxyphenyl radical or monosubstituted 4-biphenylyl or 4-phenoxyphenyl.

Of the biphenylyl substituents, most preferred is F followed by Cl. The substituents are most preferably in the 4'-position, for example, 4'-fluoro-4-biphenylyl, 4'-chloro-4-biphenylyl and 4'-bromo-4-biphenylyl, but the 2'-position is also preferred, for example, 2'-fluoro-4-biphenylyl, 2'-chloro-4-biphenylyl and 2'-bromo-4-biphenylyl. However, the biphenylyl radical can also be substituted in the 2-, 3- and/or 3'-position. Of the polysubstituted biphenylyl radicals, those which are disubstituted, particularly those disubstituted in the 2', 4'-position, are preferred, however, 3-,4-,5-,6-,7-,8- or 9-fold substitution of the biphenylyl radical is also possible. Of the polysubstituted biphenylyl radicals, those whose substituents are identical are preferred, for example, difluoro-4-biphenylyl, e.g., 2', 4'-difluoro-4-biphenylyl, dichloro-4-biphenylyl, e.g., 2',4'-dichloro-4-biphenylyl, and dibromo-4-biphenylyl, e.g., 2',4'-dibromo-4-biphenylyl. Preferred among the biphenylyl radicals bearing different substituents are those having at least one fluorine atom, for example, 2'-fluoro-4'-chloro-4-biphenylyl, 2'-fluoro-4'-bromo-4-biphenylyl, 2'-chloro-4'-fluoro-4-biphenylyl and 2'-bromo-4'-fluoro-4-biphenylyl. Preferred among the polysubstituted biphenylyl radicals are the fluorine-substituted biphenylyl radicals, for example, nonafluoro-4-biphenylyl.

Of the substituents on the 4-phenoxyphenyl radical, Cl is preferred. The substituents on the 4-phenoxyphenyl radical are preferably on the phenoxy group, particularly at the p-position, but also at the o-position. Examples of preferred substituted 4-phenoxyphenyl radicals are 4-p-chlorophenoxyphenyl, 4-o-chlorophenoxyphenyl, 4-p-fluorophenoxyphenyl and 4-p-bromophenoxyphenyl. The phenoxy group can also be substituted at the m-position. The phenyl radical (which is substituted in the 4-position by the phenoxy group) can be substituted at the 2-, 2-, 5- and/or 6-position by F, Cl and/or Br. Preferred of the polysubstituted 4-phenoxyphenyl radicals are those which are disubstituted, particularly those which are substituted in the 2- and 4-position of the phenoxy group. However, 3-, 4-, 5-, 6-, 7-, 8-, or 9-fold substitution of the 4-phenoxyphenyl radical is also possible. Preferred of the polysubstituted 4-phenoxyphenyl radicals are those substituents which are identical, for example, 4-(2,4-difluorophenoxy)-phenyl, 4-(2,4-dichlorophenoxy)phenyl, 4-(2,4-dibromophenoxy)-phenyl and 4-(pentafluorophenoxy)phenyl.

In the compounds of Formula I, n is preferably 1, i.e., the radical A preferably has 4 carbon atoms. The radical A is preferably —CH(CH$_3$)—CH$_2$—(CH$_2$)$_n$— or —C(OH)(CH$_3$)—CH$_2$(CH$_2$)$_n$—, particularly —CH(CH$_3$)—CH$_2$—CH$_2$— or —C(OH)(CH$_3$)—CH$_2$—CH$_2$—, and also, for example, —C(CH$_3$)=CH—CH$_2$—, —CH(CH$_3$)—CH$_2$—, —C(OH)(CH$_3$)—CH$_2$—, —CH(CH$_3$)—(CH$_2$)$_3$—, —C(OH)(CH$_3$)—(CH$_2$)$_3$— or —C(CH$_3$)=CH(CH$_2$)$_2$—.

When R$^1$ and/or R$^2$ are alkyl, alkyl is preferably methyl, ethyl, n-propyl or isopropyl, but also can be, for example, n-butyl, isobutyl, sec.-butyl, tert.-butyl, 1-pentyl, 2-pentyl, 3-pentyl, 2-methyl-1-butyl, 2-methyl-2-butyl, 3-methyl-1-butyl (isoamyl), 3-methyl-2-butyl, 2,2-dimethyl-1-propyl (neopentyl), 1-hexyl or 4-methyl-1-pentyl. When R$^1$ is alkyl, R$^2$ is preferably H or the same alkyl group. Azaalkyl can be R$^1$R$^2$N-alkyl and is preferably dialkylaminoalkyl, which is preferably branched and more preferably is dimethylaminoethyl, such as 2-dimethylaminoethyl, diethylaminoethyl, such as 2-diethylaminoethyl or diemthylaminopropyl, such as 2- or 3-dimethylaminopropyl. Acyl is preferably alkanoyl, and more preferably acetyl, but can also be, for example, formyl, propionyl, butyryl, isobutyryl, valeryl, isovaleryl, trimethylacetyl, methylethylacetyl, caproyl, isocaproyl, tert.-butylacetyl, diethylacetyl and nicotinoyl. When R$^1$ is acyl, R$^2$ is preferably H. Alkylene preferably is tetramethylene, 1- or 2-methyltetramethylene, pentamethylene, 1-, 2- or 3-methylpentamethylene, 1,5-dimethylpentamethylene or hexamethylene, but can also be, for example, 1- or 2-ethyltetramethylene, 1- or 2-n-propyltetramethylene, 1- or 2-isopropyltetramethylene, 1,2-, 1,3-, 1,4-, or 2,3-dimethyltetramethylene, 1,3-, 1,3-, 1,4-, 2,3-, or 2,4-dimethylpentamethylene, 1-, 2-, or 3-ethylpentamethylene and 1-, 2-, 3-, or 4-methylhexamethylene. R$^3$ is preferably H, methyl, ethyl or 2-hydroxyethyl.

Accordingly, NR$^1$R$^2$ is preferably amino, methylamino, ethylamino, n-propylamino, isopropylamino, dimethylamino, diethylamino, di-n-propylamino, diisopropylamino, 2-dimethylaminoethylamino, 2-diethylaminoethylamino, 2- or 3-dimethylaminopropylamino, acetamido, pyrrolidino, piperidino, 2-, 3- or 4-methylpiperidino, 2,6-dimethylpiperidino, homopiperidino, morpholino, piperazino, 4-methylpiperazino, 4-ethylpiperazino or 4-(2-hydroxyethyl)-piperazino.

In preferred embodiments this invention relates to compounds of Formula I wherein at least one of R, A and Z has one of the preferred values indicated above.

Examples of such preferred groups of compounds are those of Formula I wherein:

Ia : R is unsubstituted 4-biphenylyl or 4-biphenylyl monosubstituted or polysubstituted by F, Cl and/or Br;

Ib: R is 4-phenoxyphenylyl or 4-phenoxyphenylyl monosubstituted or polysubstituted by F, Cl and/or Br;

Ic: R is 4-biphenylyl, fluoro-4-biphenylyl, chloro-4-biphenylyl, bromo-4-biphenylyl, difluoro-4-biphenylyl, p-phenoxyphenyl, 4-(chlorophenoxy)-phenyl or 4-(bromophenoxy)-phenyl;

Id: R is p-biphenylyl, 2'-fluoro-4-biphenylyl, 4'-fluoro-4-biphenylyl, 4'-chloro-4-biphenylyl, 4'-bromo-4-biphenylyl, 2',4'-difluoro-4-biphenylyl, 4-p-chlorophenoxy-phenyl or 4-p-bromophenoxyphenyl;

Ie: R is p-biphenylyl, 4'-fluoro-4-biphenylyl, 4'-chloro-4-biphenylyl or 4-p-chlorophenoxy-phenyl;

If: A is —CH(CH$_3$)—CH$_2$CH$_2$—, —C(OH)(CH$_3$)—CH$_2$—(CH$_2$)$_n$— or —C(CH$_3$)=CH—CH$_2$—;

Ig: A is —C(OH)(CH$_3$)—CH$_2$—(CH$_2$)$_n$—;

Ih: A is —CH(CH$_3$)—CH$_2$CH$_2$— or —C(OH)(CH$_3$)—CH$_2$CH$_2$—;

Ii: A is —C(OH)(CH$_3$)—CH$_2$CH$_2$—;

Ij: Z is amino, diethylamino, 2-diethylaminoethylamino, acetamido, piperidino, 4-methylpiperidino, morpholino, 4-(2-hydroxyethyl)-piperazino, imidazol-1-yl, phthalimido or 3,4-dihydro-4-oxo-phthalazin-1-ylamino;

Ik: Z is amino, diethylamino, acetamido, piperidino, morpholino, imidazol-1-yl or phthalimido;

Il: Z is amino;

Im: Z is morpholino;

In: Z is phthalimido;

Io: R is 4-biphenylyl or 4-biphenylyl monosubstituted or polysubstituted by F, Cl and/or Br.,
A is (CH(CH$_3$)—(CH$_2$)$_2$—, —C(CH$_3$)=CHCH$_2$— or —C(OH)(CH$_3$)—(CH$_2$)$_2$— and
Z is amino;

Ip: R is p-biphenylyl, 2'-fluoro-4-biphenylyl, 4'-fluoro-4-biphenylyl, 4'-chloro-4-biphenylyl, 4'-bromo-4-biphenylyl, 2',4'-difluoro-4-biphenylyl, 4-p-chlorophenoxy-phenyl or 4-p-bromophenoxy-phenyl,
A is —CH(CH$_3$)—(CH$_2$)$_2$—, —C(OH)(CH$_3$)—CH$_2$—(CH$_2$)$_n$— or —C(CH$_3$)=CH—CH$_2$—, and
Z is amino diethylamino, 2-diethylaminoethylamino, acetamido, piperidino, 4-methylpiperidino, morpholino, 4-(2-hydroxyethyl)-piperazino, imidazol-1-yl, phthalimido or 3,4-dihydro-4-oxo-phthalazin-1-ylamino;

Iq: R is p-biphenylyl, 2'-fluoro-4-biphenylyl, 4'-fluoro-4-biphenylyl, 4'-chloro-4-biphenylyl, 4'-bromo-4-biphenylyl or 2',4'-difluoro-4-biphenylyl,
A is —CH(CH$_3$)—(CH$_2$)$_2$—, —C(OH)(CH$_3$)—CH$_2$—(CH$_2$)$_n$— or —C(CH$_3$)=CH—CH$_2$—, and
Z is amino, diethylamino, 2-diethylaminoethylamino, acetamido, piperidino, 4-methylpiperidino, morpholino, 4-(2-hydroxyethyl)-piperazino, imidazol-1-yl, phthalimido or 3,4-dihydro-4-oxo-phthalazin-1-ylamino;

Ir: R is 4-p-chlorophenoxy-phenyl or 4-p-bromophenoxyphenyl,
A is —CH(CH$_3$)—(CH$_2$)$_2$ or —C(OH)(CH$_3$)—(CH$_2$)$_2$—, and
Z is amino, piperidino, 4-methylpiperidino, morpholino or phthalimido;

Is: R is p-biphenylyl, 4'-fluoro-4-biphenylyl, 4'-chloro-4-biphenylyl or 4-p-chlorophenoxy-phenyl,
A is —CH(CH$_3$)—(CH$_2$)$_2$— or —C(OH)(CH$_3$)—(CH$_2$)$_2$—, and
Z is amino, diethylamino, acetamido, piperidino, morpholino, imidazol-1-yl or phthalimido;

It: R is p-biphenylyl, 4'-fluoro-4-biphenylyl, 4'-chloro-4-biphenylyl or 4-p-chlorophenoxy-phenyl,
A is —CH(CH$_3$)—(CH$_2$)$_2$— or —C(OH)(CH$_3$)—(CH$_2$)$_2$—, and
Z is amino.

In a process aspect, this invention relates to a process for the preparation of the compounds of Formula I and their physiologically acceptable acid addition salts, which comprises (a) treating a compound of the general formula II $$R—Q \qquad \text{II}$$

wherein Q is a radical which can be reduced to the group —A—Z, and R, A and Z have the values given above, with a reducing agent; or (b) treating a compound which otherwise corresponds to the general Formula I but wherein the amino group and/or the hydroxyl group is present in a functionally modified form, with a solvolyzing agent; or (c) reacting a compound of the general Formula III $$R—E \qquad \text{III}$$

wherein E is —C(CH$_3$)(OH)—(CH$_2$)$_m$—CH=CH$_2$, —CH(CH$_3$)—(CH$_2$)$_m$—CH=CH$_2$ or —A—X, m is 0 or 1, X is Cl, Br, I, OH or OH which is functionally modified in a reactive manner, and R and A have the values given above, with a compound of the general formula H-Z or with a reactive derivative of such a compound; or (d) treating an amine of the general Formula IV $$R—A—N(CH_2CH_2OH)—CH_2CH_2X \qquad \text{IV}$$

wherein R, A and X have the values given above, with an agent which splits off HX; or (e) reacting an amine of the general Formula V $$R—A—N(CH_2CH_2X)_2 \qquad \text{V}$$

wherein R, A and X have the values given above, with a compound of the general Formula H$_2$NR$_3$; or (f) diazotizing a compound of the general Formula VI $$R^4—A—Z \qquad \text{VI}$$

wherein R$^4$ is a 4-biphenylyl or 4-phenoxyphenyl monosubstituted or polysubstituted by NH$_2$ and, if appropriate, additionally monosubstituted or polysubstituted by F, Cl and/or Br, and A and Z have the values given above, and then treating the resulting diazonium salt with a halogenating agent; or (g) reacting a compound of the general Formula VII $$Q^1—R^5—A—Z \qquad \text{VII}$$

or a salt thereof, with a compound of the general Formula VIII $$R^6—Q^2 \qquad \text{VIII}$$

or with a salt thereof, wherein one of Q$^1$ and Q$^2$ is OH and the other is X, R$^5$ is p-phenylene or p-phenylene monosubstituted or polysubstituted by F, Cl and/or Br, R$^6$ is phenyl or phenyl which is monosubstituted or polysubstituted by F, Cl and/or Br, and A, Z and X have the values given above, and, if appropriate, a thus-produced hydroxy compound of Formula I [A=—C(OH)(CH$_3$)—CH$_2$—(CH$_2$)$_n$-] is treated with a dehydrating agent, and/or a thus-produced compound of Formula I [A = —C(OH)(CH$_3$)—CH$_2$—(CH$_2$)$_n$— or —C(CH$_3$)=CH—(CH$_2$)$_n$—], is treated with a reducing agent, and/or in a thus-produced compound of Formula I one or more chlorine atoms or bromine atoms are introduced by treatment with chlorinating or brominating agents, and/or in a thus-produced compound of Formula I radical Z is converted into another Z radical by treatment with an alkylating, acylating, solvolyzing and/or reducing agent, and/or a thus-produced free base of Formula I is converted into a physiologically acceptable acid addition salt thereof by treatment with an acid.

In other respects the preparation of the compounds of Formula I is carried out in accordance with methods which are in themselves known, such as are described in the literature (for example, in the standard works such as Houben-Weyl, Methoden der organischen Chemie ("Methods of Organic Chemistry"), Georg-ThiemeVerlag, Stuttgart), and under the reaction conditions which are known and suitable for the reactions mentioned. In the course thereof, it is also possible to make use of variants which are in themselves known and are not mentioned here in greater detail.

In all the general formulae in the preceding and following text, R, A and Z have the values given for Formula I unless otherwise expressly indicated.

The starting compounds for the preparation of the compounds of Formula I are, in part, known. They can be prepared by processes which are in themselves known. If desired, the starting compounds can also be formed in situ and are not isolated from the reaction mixture but are immediately reacted further to give a compound of Formula I.

In the compounds of Formula II, the radical Q is preferably the group —A$^1$—Y wherein A$^1$ is —CH(CH$_3$)—(CH$_2$)$_n$—, —C(CH$_3$)=CH—(CH$_2$)$_m$— or —C(OH)(CH$_3$)—(CH$_2$)$_n$—, m is 0 or 1, and Y is CN, CONR$^1$R$^2$, CH$_2$NO$_2$, CH$_2$N$_3$, CH$_2$NR$^1$—W (wherein W is a benzyl group or another radical which can be split off by hydrogenolysis), CH$_2$N(W)$_2$, CH=NOH, CHOH—NR$^1$R$^2$, CH=NR$^1$, CH$_2$NR$^7$ (wherein R$^7$ is alkylidene or azaalkylidene in each case of 1 - 6 carbon atoms, oxo-alkylene of 4 - 7 carbon atoms, oxo-3-oxapentamethylene or oxo-3-R$^3$-3-azapentamethylene) or another radical which can be reduced to give a CH$_2$—NR$^1$R$^2$ group. In addition, the group Q can, for example, be —C(=CH$_2$)—(CH$_2$)$_{n+1}$—Z, —C(=CH$_2$)—(CH$_2$)$_n$—Y, —CH(CH$_3$)—CH=CH—Z, —CH(CH$_3$)—CH=CH—Y, —C(OH)(CH$_3$)—CH=CH—Z, —C(OH)(CH$_3$)—CH=CH—Y, —C(=CH$_2$)—CH=CH—Z or —C(=CH$_2$)—CH=CH—Y.

The starting compounds of Formula II are, in general, new. They can, however, be prepared analogously to known processes. Thus, the acid amides of the formula R—C(OH)(CH$_3$)—(CH$_2$)$_p$—CONR$^1$R$^2$ ($p$ = 1 or 2) can be obtained, for example, by Friedel-Crafts acetylation of the biphenyls or diphenyl ethers of the formula R-H to give the ketones of the formula R-COCH$_3$, a Reformatsky reaction to give the hydroxy-esters of the formula R—C(OH)(CH$_3$)—(CH$_2$)$_p$—COOC$_2$H$_5$ and reaction with a compound of the formula HNR$^1$R$^2$. Elimination of water leads to the unsaturated amides of the formula R—C(CH$_3$)=CH—(CH$_2$)$_m$—CONR$^1$R$^2$ and reduction leads to the saturated amides of the formula R—CH(CH$_3$)—(CH$_2$)$_p$—CONR$^1$R$^2$. Reduction of the hydroxy-esters mentioned, using HI, gives with simultaneous saponification, acids of the formula R—CH(CH$_3$)—(CH$_2$)$_p$—COOH, which can be converted by means of LiAlH$_4$ into the corresponding alcohols of the formula R—CH(CH$_3$)—(CH$_2$)$_p$—CH$_2$OH. Alcohols of the formula R—C(OH)(CH$_3$)—(CH$_2$)$_p$—CH$_2$OH can be obtained by reducing the abovementioned hydroxy-esters with LiAlH$_4$, and alcohols of the formula R—C(CH$_3$)=CH—(CH$_2$)$_p$—OH can be obtained by dehydration and subsequent reduction of the hydroxy-esters. Reacting the ketones of the formula R—CO—CH$_3$ with KCN gives the cyanohydrins of the formula R—C(OH)(CH$_3$)—CN, which can be hydrolyzed to give the amides of the formula R—C(OH)(CH$_3$)—CONH$_2$ or the hydroxy acids of the formula R—C(OH)(CH$_3$)—COOH. Reduction of the hydroxy acids by various methods gives the acids of the formula R—CH(CH$_3$)—COOH, the glycols of the formula R—C(OH)(CH$_3$)—CH$_2$OH and the alcohols of the formula R—CH(CH$_3$)—CH$_2$OH. From the alcohols mentioned, it is possible to prepare, in a conventional manner, for example using SOCl$_2$ or PBr$_3$, the corresponding halides, which can be converted, using alkali metal nitrites, into the corresponding nitro compounds of the formula R—A$^1$—CH$_2$NO$_2$, using alkali metal azides, into the azides of the formula R—A$^1$—CH$_2$N$_3$, or using amines of the formula W—NH$_2$ (for example, benzylamine) or (W)$_2$NH, into amines of the formula R—A$^1$—CH$_2$—NH—W or R—A$^1$—CH$_2$N(W)$_2$. Oxidation of the alcohols leads to the corresponding aldehydes of the formula R—A$^1$—CHO, which can be converted, using hydroxylamine, into the corresponding oximes of the formula R—A$^1$—CH=NOH and, using compounds of the formula HNR$^1$R$^2$, into the corresponding aldehyde-ammonias of the formula R—A$^1$—CHOH—NR$^1$—R$^2$ or imines of the formula R—A$^1$—CH=NR$^1$. Unsaturated nitriles of the formula R—C(CH$_3$)=CH—CN can be prepared, for example, from the ketones mentioned, of the formula R—COCH$_3$, and cyanoacetic acid.

Among the starting compounds of Formula II, amides of the formula R—A$^1$—CONR$^1$R$^2$ and nitriles of the formula R—A$^1$—CN are preferred.

The starting compounds of Formula II can be converted into compounds of Formula I, for example, by catalytic hydrogenation or with nascent hydrogen, with complex metal hydrides or with other chemical reducing agents. The methods of reduction which are the most suitable for the indivdual starting materials generally depend on the nature of the functional group Y and are familiar to the expert from the data of the literature. Thus, nitriles, amines of the formulae R—A—NH—W or R—A—N(W)$_2$, oximes and aldehyde-ammonias, for example can be hydrogenated catalytically with particular advantage. On the other hand, the acid amides are reduced particularly advantageously with complex metal hydrides or with diborane.

Noble metal catalysts, nickel catalysts or cobalt catalysts, for example, and also mixed catalysts, such as copperchromium oxide, are suitable for catalytic hydrogenations. Noble metals which can be used are primarily platinum and palladium, which can be present on supports (for example, on charcoal, calcium carbonate or strontium carbonate), in the form of oxides (for example, platinum oxide) or in a finely divided form. Nickel catalysts and cobalt catalysts are preferable employed as Raney metals. Hydrogenation can be carried out preferably at pressures of about 1 to 200 atms. and at temperatures of about $-80°$ to $+150°$, preferably 20° to 100°. The hydrogenation is carried out in the presence of an inert solvent, for example, an alcohol, such as methanol, ethanol or isopropanol, or carboxylic acid, such as acetic acid, an ester, such as ethyl acetate, or an ether, such as tetrahydroguran (THF) or dioxane. It is also possible to use solvent mixtures, including mixtures containing water. In addition, it can be advantageous to add a base, such as sodium hydroxide or potassium hydroxide or ammonia, when hydrogenating, for example, when hydrogenating nitriles.

Complex metal hydrides, such as $LiAlH_4$, $NaBH_4$ or $NaAl—(OCH_2CH_2OCH_3)_2H_2$, and diborane can be employed as reducing agents, if desired with the addition of a catalyst such as $BF_3$, $AlCl_3$ or $LiBr$. Suitable solvents for this purpose are, in particular, ethers, such as diethyl ether, THF, dioxane, 1,2-dimethoxyethane or diglyme, and hydrocarbons, such as benzene. Solvents suitable for reductions with $NaBH_4$ are, above all, alcohols, such as methanol or ethanol. In this method it is preferable to reduce at temperatures of about $-80°$ to $+150°$, particularly about 20° to 120°.

A further suitable method of reduction is with nascent hydrogen. This can be produced, for example, by treating metals with acids or bases. For example, the systems zinc/acid, zinc/alkali metal hydroxide solution, iron/acid and tin/acid can be used. Examples of suitable acids are hydrochloric acid and/or acetic acid. An alkali metal such as sodium, in an alcohol, such as ethanol, isopropanol, n-butanol, amyl alcohol or isoamyl alcohol, or in phenol can also be used as the reducing agent, and also, for example, an aluminum-nickel alloy in an alkaline aqueous solution or alkaline aqueous-alcoholic solution, as well as sodium amalgam or aluminium amalgam in an aqueous-alcoholic solution or aqueous solution. The reaction temperatures in these methods are about 0° to about 150°, preferably about 20° to 120°.

The starting compounds of Formula II can also be converted into compounds of Formula I by cathodic reduction, preferably in an aqueous-alcoholic or aqueous acetic acid medium. Examples of other suitable reducing agents are sodium dithionite in an aqueous-alcoholic or alkaline solution, and also iron-II hydroxide, tin-II chloride, hydrogen sulfide, hydrogen sulfides, sulfides, polysulfides and hydrazine, all of which can be used in accordance with conditions indicated in the literature for reductions of this kind.

Selective reductions are also possible by selection of reagents and reaction conditions. Thus, Schiff's bases which contain a C—C double bond in the radical $A^1$, can be reduced, using $LiAlH_4$, to give the corresponding unsaturated amines.

The compounds of Formula I can also be obtained by solvolysis, preferably hydrolysis, from starting materials which otherwise, correspond to Formula I but wherein the amino group and/or the hydroxyl group is present in a functionally modified form.

The starting compounds of the solvolysis are, in general, new, but they can be prepared analogously to methods which are in themselves known. Examples of these starting materials are acyl derivatives of the amines of Formula I, particularly the amides of the formula $R—A—NR^1—Ac$ (wherein Ac is any desired acyl radical, other than $R^2$, the nature of which is not critical, since it is split off in the solvolysis, but which preferably is of 7 - 10 carbon atoms, for example, aroyl of up to 10 carbon atoms, such as benzoyl). The amides mentioned can also be obtained, for example, by Friedel-Crafts alkylation of the biphenyls of the formula R—H, using halogeno-amides of the formula $Cl—A—NR^1—Ac$ or $Br—A—NR^1—Ac$. Other starting compounds are isocyanates of the formula R—A—NCO, which are formed as non-isolated intermediate products in the Hofmann degradation of corresponding acid amides of the formula $R—A—CONH_2$, in the Curtius degradation of corresponding azides of the formula $R—A—CON_3$, in the Lossen degradation of corresponding hydroxamic acids of the formula R—A—CO—NHOH or in the Schmidt degradation of corresponding carboxylic acids of the formula R—A—COOH. The carboxylic acids of the formula R—A—COOH on which the starting materials for these degradation reactions are based, can be obtained, for example, by Friedel-Crafts acylation of the biphenyls or diphenyl ethers of the formula R—H, using succinic anhydride, to give the keto-acids of the formula $R—COCH_2CH_2COOH$, and subsequent reaction with methylmagnesium iodide to give hydroxy acids of the formula $R—C(OH)(CH_3)—CH_2CH_2COOH$ and, if desired, subsequent dehydration and/or reduction.

Examples of starting compounds for the solvolysis in which the OH group is functionally modified, are the corresponding alcoholates, particularly the magnesium alcoholates or lithium alcoholates, such as are formed as reaction products in Grignard reactions or in reactions with organolithium compounds, the esters (for example, the carboxylic acid esters wherein the carboxylic acid radical preferably is of up to 7 carbon atoms, for example, acetyl or benzoyl, the alkylsulphonic or arylsulphonic acid esters wherein the alkyl radical preferably is of 1 - 6 carbon atoms and the aryl radical preferably is of 6 - 10 carbon atoms) and the ethers (for example, the alkyl ethers wherein alkyl preferably is of up to 6 carbon atoms, the aryl ethers wherein aryl preferably is of 6 - 10 carbon atoms, and the aralkyl ethers wherein aralkyl preferably is of 7 - 11 carbon atoms). The boric acid esters which are intermediately formed in the oxidative hydroboronation, can, for example, also be used. In addition, a chlorine atom or iodine atom can be used instead of the hydroxyl group, the corresponding hydrogen halide acid esters then being present.

The magnesium alcoholates mentioned can be obtained, for example, by reacting ketones of the formula $R—CO—(CH_2)_{n+1}—Z$ with methyl magnesium iodide or by reacting arylmagnesium halides of the formula R-MgCl or R-MgBr with ketones of the formula $CH_3CO—(CH_2)_{n+1}—Z$. Halides of the formula $R—CBr(CH_3)—(CH_2)_{n+1}—Z$ or $R—CCl(CH_3)—(CH_2)_{n+1}—Z$ can be prepared, for example, by halogenation of acid amides of the formula R—A—COZ and subseqeunt reduction with $LiAlH_4$. The corresponding esters of the formula $R—C(OAc)(CH_3)'(CH_2)_{n+1}—Z$ can be prepared from the halides by reaction with potassium acylates, for example, potassium acetate.

The solvolysis of these compounds is preferably carried out by the action of a solvent such as water (hydrolysis) or an alcohol preferably of 1 - 4 carbon atoms (alcoholysis) in the presence of an acid or basic catalyst, for example, a mineral acid, such as sulfuric acid or hydrochloric acid, a metal hydroxide, such as sodium hydroxide, potassium hydroxide, calcium hydroxide, barium hydroxide, lead hydroxide or silver hydroxide, or a metal salt or ammonium salt, such as sodium carbonate or potassium carbonate or ammonium chloride. Methanol, ethanol or isopropanol are preferably used as the alcohol, alone or as a mixture with water. The solvolysis is preferably carried out at temperatures of about 0° to about 120°.

The amides mentioned above are preferably hydrolyzed by boiling for several hours with aqueous, aqueous-alcoholic or alcoholic hydrochloric acid, sulfuric acid, sodium hydroxide solution or potassium hydroxide solution. The magnesium alcoholates mentioned are preferably not isolated but, instead, after being formed in the Grignard reaction, are hydrolyzed in situ using a dilute acid, for example, suluric acid or hydrochloric acid, or using aqueous ammonium chloride solution. The halides and esters mentioned are preferably saponified in an aqueous or aqueous-alcoholic solution or suspension, and, if desired, a solubilizer can be present, for example, an alcohol, glycol or gylcol ether. Alkalies such as NaOH or KOH are preferably used as the saponifying agent.

The compounds of Formula I can also be obtained by reacting a compound of the formula R-E(III) with a compound of the formula H-Z or with a reactive derivative of such a compound, for example, a metal derivative (such as potassium phthalimide). The starting compounds of formula III are new. They can be prepared, for example, by a Grignard reaction of ketones of the formula $R—CO—(CH_2)_{n+1}—X$ with $CH_3MgI$, to give carbinols of the formula $R—C(OH)(CH_3)—(CH_2)_{n+1}—X$ and, if desired subsequent dehydration and/or elimination of HX and/or reduction. The starting compounds of the formula H-Z are, in general, known.

The reaction of compounds of Formula III with compounds of the formula H-Z is preferably carried out at temperatures of about 0° to about 250°, preferably about 50° to 120°, and at pressures of about 1 to about 50 atms. The reaction can be carried out in the presence of an inert solvent, for example, an alcohol, such as methanol, ethanol, isopropanol or n-butanol, an ether, such as diethyl ether, diisopropyl ether, THF or dioxane, a hydrocarbon, such as benzene, toluene or xylene, an amide, such as dimethylformamide (DMF), or a sulfoxide, such as dimethylsulfoxide. If desired, a catalyst can be present, for example, sodium amide, which can also be produced in situ from sodium and liquid ammonia, and also bases, such as sodium carbonate, potassium carbonate, sodium bicarbonate or potassium bicarbonate. It is also possible to use an excess of the compound of the formula H—Z as the solvent, preferably at the boiling point. If the radical E in Formula III is the group —A—X, X is preferably Cl, Br or I. If X is an OH group which is functionally modified in a reactive manner, it preferably is alkylsulfonyloxy or arylsulfonyloxy preferably of up to 10 carbon atoms. Secondary amines of the formula R—A—NHalkyl can also be prepared by heating alcohols of the formula R—A—OH with alkylamines in the presence of Raney nickel.

Morpholine derivatives of Formula I (Z=morpholino) can also be obtained by elimination of HX from amines of Formula IV. The amines of Formula IV are new. They can be obtained, for example, by reacting halogen compounds of the formula R-A-Cl or R—A—Br with amines of the formula $HN(CH_2CH_2OH)—CH_2CH_2X$, for example diethanolamine. In the compounds of Formula IV, X is preferably OH. Dehydration of diols of this kind can be carried out, for example, by the action of an acid catalyst, such as sulfuric acid or a sulfonic acid, such as p-toluenesulfonic acid, in an inert solvent, for example a hydrocarbon, such as benzene, toluene or xylene, at temperatures of about 0 to about 150°. If the radical X in the compounds of Formula IV is a halogen atom or an OH group which is functionally modified in a reactive manner, the elimination of HX is preferably carried out, however, by the action of a base, such as NaOH, or KOH, preferably in an alcoholic or aqueous-alcoholic medium at temperatures of about 0° to about 100°.

Piperazine derivatives of Formula I (Z = a piperazino group which is unsubstituted in the 4-position or which is substituted by alkyl or hydroxyalkyl in each case of up to 6 carbon atoms) can also be obtained by reacting an amine of Formula V with a compound of the formula $H_2NR^3$ (for example, ammonia, methylamine or 2-hydroxyethylamine). The compounds of Formula V (which include the compounds of Formula IV) are new. They can be prepared from halogen compounds of the formula R—A—Cl or R—A—Br by reaction with amines of the formula $HN(CH_2CH_2X)_2$ (for example, diethanolamine), and, if desire, OH groups which may be present can subsequently be converted into other X groups by reaction with, for example, $SOCl_2$ or $PBr_3$. The reaction of amines of Formula V with the compounds of the formula $H_2NR^3$ is as a rule carried out in the presence of an inert solvent, such as benzene, toluene or xylene, at temperatures of about 0° to about 150°, and a catalyst, for example, a strong acid, such as sulfuric acid or an organic sulfonic acid, can be added.

Halogen-containing compounds of Formula I can be obtained from the corresponding amino compounds of Formula VI by first diazotizing the latter, for example, by reacting with a salt or an ester of nitrous acid (such as $NaNO_2$ or n-butyl nitrite) in aqueous hydrochloric acid at temperatures of about $-20°$ to $+10°$, and subsequently converting the resulting diazonium salt into the desired halogen compound of Formula I. Thus, the corresponding fluorine compounds are preferably obtained by reacting the diazonium salt with $HBF_4$ to give the diazonium tetrafluoborate and subsequent thermal decomposition at about 100° to 200° in the absence or presence of an inert solvent, such as toluene, xylene or dioxane. Decomposition at room temperature in an aqueous medium in the presence of copper powder is also possible. If the diazotization is carried out using $NaNO_2$ in anhydrous hydrofluoric acid, the desired fluorine compound is obtained directly by subsequent warming. Replacement of the diazonium group by chlorine or bromine is preferably carried out in a hot aqueous solution in the presence of $Cu_2Cl_2$ or $Cu_2Br_2$. The starting compounds of Formula VI can be obtained, for example, by reducing the corresponding nitro compounds and these in turn can be obtained by nitrating the corresponding unsubstituted compounds of Formula I.

Diphenyl ether derivatives of Formula I (R= unsubstituted or substituted 4-phenoxyphenyl) can also be prepared by reacting a compound of Formula VII or a salt of such a compound, with a compound of Formula VIII or a salt of suc a compound. The starting compounds of Formula VII can be prepared, for example, by reacting halogen compounds of the formula $Q^1$-$R^5$—A—Cl or $Q^1$—$R^5$—A—Br with compounds of the formula HZ. The starting compounds of Formula VII are, in general, known. It is possible either to react a phenol of Formula VII ($Q^1$ = OH) with a compound of Formula VIII ($Q^2$ = X) or to react a compound of Formula VII ($Q^1 = X$) with a phenol of Formula VIII ($Q^2 = OH$).

In this reaction, the phenols are preferably in the form of the corresponding phenolates, particularly the corresponding sodium phenolates or potassium phenolates. The reaction is preferably carried out in the presence of an inert solvent, such as DMF or phosphoric acid hexamethyltriamide (HMPT), in the presence of a catalyst, such as copper powder, at a temperature of about 50 to about 200, preferably 80° to 130°.

If desired, a resulting hydroxy compound of the formula $R-C(OH)(CH_3)-CH_2-(CH_2)_n-Z$ can be dehydrated to give the corresponding unsaturated compound of the formula $R-C(CH_3)=CH-(CH_2)_n-Z$, preferably by the action of an acid catalyst, such as sulfuric acid or a sulfonic acid, such as p-toluenesulfonic acid, in an inert solvent, for example, a hydrocarbon, such as benzene or toluene, at temperatures of about 0° to about 150°, preferably 80° to 110°.

In addition, it is possible, if desired, to reduce the hydroxy compounds mentioned above, of the formula $R-C(OH)(CH_3)-CH_2-(CH_2)_n-Z$, and unsaturated compounds of the formula $R-C(CH_3=CH-(CH_2)_n-Z$ to the saturated compounds of the formula $R-CH(CH_3)-CH_2-(CH_2)_n-Z$. The reduction of the hydroxy compounds is carried out, for example, with hydriodic acid, preferably in acetic acid at temperature of 20° to (preferably) the boiling point. The unsaturated compounds can be hydrogenated, preferably catalytically under the condtions indicated above, for example, over a noble metal catalyst, such as palladium-on-charcoal, at room temperature and ambient pressure.

In addition, one or more chlorine atoms or bormine atoms can be introduced into a thus-produced compound of Formula I by halogenation in accordance with methods described in the literature. This is possible, for example, by direct reaction with elementary chlorine or bromine in an inert solvent, such as ether, tetrachloromethane or acetic acid, optionally in the presence of a catalyst such as iron filings, iodine or $AlCl_3$, preferably at temperatures of about −30° to 100°.

In addition, the radical Z in a resulting compound of Formula I can be converted into another Z radical by alkylation, acylation, solvolysis and/or reduction.

For example, a resulting primary amine (I, Z = $NH_2$) or secondary amine (I, Z = NHalkyl) can be converted into a secondary or tertiary amine of Formula I by treatment with an alkylating agent. Examples of suitable alkylating agents are compounds of the formulae $R^1-X$, $R^2-X$ or, optionally, $X-R^1R^2-X$, for example, methyl chloride, methyl bromide, methyl iodide, diemthyl sulfate, p-toluenesulfonic acid methyl ester, ethyl chloride, ethyl bromide, ethyl iodide, diethyl sulfate, n-propyl chloride, bromide or iodide and the like, as well as 1,4-dichlorobutane, 1,4-dibromobutane, 1,4-diiodobutane, 1,5-dichloropentane, 1,5-dibromopentane or 1,5-diiodopentane, or 2,2'-dichloro-, 2,2'-dibromo and 2,2'-diiodo-diethyl ether. It is also possible to condense with aldehydes or ketones with the formation of aldehyde-ammonia compounds or Schiff's bases and subsequently either to hydrogenate these are indicated above or to treat them with an alkylating agent and subsequently hydrolyze the resulting quaternary salt. For example, a primary amine can be converted, by condensation with benzaldehyde, into the N-benzylidene compound and the latter can be converted, with an alkyl halide, into one of its quaternary salts, which can subsequently be converted into the secondary amine, for example, by treatment with aqueous alcohol, with the elimination of benzaldehyde. It is also possible to alkylate, using aldehydes or ketones under reducing conditions, the corresponding aldehydeammonias formed as intermediate products. For example, one or two methyl group can be introduced by means of formaldehyde in the presence of formic acid. In addition, it is possible to alkylate in the presence of Raney nickel, using an alcohol of 1 - 6 carbon atoms. The alkylation is preferably carried out in the presence or absence of one of the inert solvents mentioned, at temperatures of about 0° to about 120°, preferably 40° to 100°, and a catalyst, preferably a base, such as potassium tert.-butylate, can also be present.

Suitable acylating agents for acylating resulting primary or secondary amines of Formula I are preferably the halides (for example, chlorides or bromides) or anhydrides of carboxylic acids of 1 - 6 carbon atoms, for example, acetic anhydride, propionyl chloride, isobutyryl bromide, formic acid-acetic acid anhydride or phthalic anhydride. The addition of a base, such as pyridine or triethylamine, in the acylation is possible, but not necessary. The acylation is preferably carried out in the presence or absence of one of the invert solvents mentioned, for example, benzene, at temperatures of about 0° to about 160°, preferably about 20° to 120°.

The radical Z in a resulting compound of Formula I (Z = phthalimido or $NR^1$-acyl) can be converted into another Z radical (particularly Z = $NHR^1$ or 3,4-dihydro-4-oxo-phthalazin-1-yl-amino), by solvolysis. Thus, the imides and amides of Formula I mentioned above can be hydrolyzed under the conditions indicated above, preferably using aqueous, aqueous-alcoholic or alcoholic hydrochloric acid, sulfuric acid, sodium hydroxide solution or potassium hydroxide solution, at temperatures of about 0° to about 120°, preferably at the boiling point.

A special embodiment of the solvolysis is the hydrazinoysis of the phthalimido compounds of Formula I, which can be converted into the dihydrophthalazin-4-ones mentioned above with hydrazine, preferably in the form of hydrazine hydrate in alcoholic or aqueous-alcoholic solution at temperatures of about 20° to 80°. These dihydrophthalazin-4-ones can be hydrolyzed to give amines of Formula I (Z — $NH_2$) under milder conditions than the corresponding phthalimides, for example, by treatment of a short time with aqueous-alcoholic mineral acid, preferably aqueous-ethanolic hydrochloric acid, at temperatures of 50°0 to 80°.

In addition, it is possible to reduce an acyl group in the Z radical to give the corresponding alkyl group, by one of the methods indicated above, preferably using a complex metal hydride, such as $LiAlH_4$.

A resulting base of Formula I can be converted in the customary manner, using an acid, into the appropriate acid addition salt. Acids which can be used for this reaction are those which give physiologically acceptable salts. Thus, inorganic acids can be used, for example, sulfuric acid, hydrogen halide acids, such as hydrochloric acid or hydrobromic acid, phosphoric acids, such as orthophosphoric acid, nitric acid and sulphamic acid and also organic acids, in detail, aliphatic, alicyclic, araliphatic, aromatic or heterocyclic, monobasic or polybasic carboxylic or sulfonic acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicyclic acid, 3-phenylpropionic acid, citric acid, gluconic acid, ascorbic acid, nicotinic acid, isonicotinic acid, methanesulfonic acid ethanesulfonic acids, ethanedisulfonic acid, 2-hydroxyethanesulfonic acid, benzenesulfonic acid, p-toluenesulfonic acid and naphthalene-monosulfonic and -disulfonic acids.

If desired, the free bases of Formula I can be liberated from their salts by treatment with a strong base, such as sodium hydroxide or potassium hydroxide or sodium carbonate or potassium carbonate.

The compounds of Formula I can contain one or more centers of asymmetry. In this case, they are usually obtained in the racemic form. These racemates can be resolved into their optical antipodes, mechanically or chemically, in accordance with methods which are in themselves known. Preferably, diastereomers are formed from the racemic mixture by reaction with an optically active resolving agent. Examples of suitable resolving agents are optically active acids, such as the D- and L-forms of tartaric acid, diacetyltartaric acid, dibenzoyltartaric acid, mandelic acid, malic acid, lactic acid or the various optically active camphorsulfonic acids, such as β-camphorsulfonic acid.

It is, of course, also possible to obtain optically active compounds of Formula I by the methods described above, by using optically active starting compounds.

The compounds of Formula I and their physiologically acceptable acid addition salts are well tolerated and possess valuable pharmacological properties. In particular, they possess antiphlogistic activity which can be demonostrated in rats, for example, in the Adjuvantarthritis test by the method of Newbould (Brit. J. Pharmacol. 21. (1963) pages 127 - 136). They also possess anti-arteriosclerotic activity, cholesterol serum-level lowering activity (demonstrable in the serum of rats by the method of Levine et al., Automation in Analytical Chemistry, Technicon Symposium 1967, Mediad, New York, pages 25 - 28), triglyceride serum level lowering activity (demonstrable by the method of Noble and Campbell, Clin. Chem. 16 (1970), pages 166 - 170 ), as well as, analgesic, antipyretic, enzyme-inducing and fibrinolytic activity and activity which inhibit the aggregation of thrombocytes can be observed by methods which are currently employed for these purposes.

The compounds of Formula I and their physiologically acceptble acid addition salts can be used as medicaments and also as intermediate products for the preparation of other medicaments. For example, the primary amines of the formula I (Z = NH$_2$) can be converted, by reaction with nitrous acid, into the corresponding alcohols and, by the oxidation of the latter, into the corresponding carboxylic acids, which possess antiphlogistic activity.

The compounds of Formula I and their physiologically acceptable acid addition salts can be used, mixed with solid, liquid and/or semi-liquid medicinal excipients, as medicaments in human and veterinary medicine. Excipients which can be used are organic or inorganic substances which are suitable for enteral or parenteral administration or topical application and which do not react with the active compounds, for example, water, vegetable oils, benzyl alcohols, polyethylene glycols, gelatine, lactose, starch, magnesium stearate, talc, petroleum jelly or cholesterol. Tablets, dragees, capsules, syrups, elixirs, drops or suppositories are used in particular, for enteral administration, solutions, preferably oily or aqueous solutions, and suspensions, emulsions or implants are used for parenteral administration, and ointments, creams or powders are used for topical application. The new compounds can also be lyophilized and the resulting lyophilizates can be used, for example, for the production of injection preparations. These preparations can be sterilized and/or can contain auxiliary substances such as lubricants, preservatives, stabilizers and/or wetting agents, emulsifiers, salts for controlling the osmotic pressure, buffer substances, colorants, flavorings and/or aroma substances. if desired, they can also contain one or more other active compounds, for example, one or more vitamins.

The novel compounds can be administered analogously to known, commercially available antiphlogistics, preferably in dosages of about 10 to 1,000 mg. particularly 30 to 300 mg, per dosage unit. The daily dosage is preferably about 0.2 to 20 mg/kg of body weight. The particular dose for each patient depends on diverse factors, for example, on the activity of the particular compound employed, on age, body weight, the general condition of health, sex, the diet, the point in time, and means, of administration, the rate of elimination, the combination of medicaments and the severity of the particular illness, and can be determined by conventional medical techniques. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The compounds of Formula I of the following examples are particularly suitable for the production of pharmaceutical preparations.

In the following examples, "customary working up" denotes the following: if necessary, water is added, or dilute sodium hydroxide solution is added, if the product is a base, the mixture is extracted with an organic solvent which is immiscible with water (for example, benzene, choroform or dichloromethane), the phases are separated and the organic phase is dried over sodium sulfate, filtered, evaporated and purified by chromatography and/or crystallization. If the product is basic, it can also be purified by crystallizing one of its acid addition salts. Temperatures are degrees Celsius.

EXAMPLE 1

A solution of 23.9 g of 3-p-biphenylyl-butyramide [m.p. 156°- 158°' obtainable by Friedel-Crafts acetylation of biphenyl to give 4-acetylbiphenyl (m.p. 118°- 120°), reaction with bromoacetic acid ethyl ester/zinc to give 3-p-biphenylyl-3-hydroxy-butyric acid ethyl ester (m.p. 55°- 56°), treatment with HI/acetic acid, reaction of the resulting 3-p-biphenylyl-butyric acid (m.p. 118°- 12-°) with SOCl$_2$ to give the chloride, and reaction with ammonia] in 500 ml of THF is added dropwise, while stirring, to a suspension of 7.6 g of LiAlH$_4$ in 250 ml of absolute THF, the mixture is boiled for 16 hours, ethyl acetate is added, with cooling, followed by 32% sodium hydroxide solution and the mixture is worked up in the customary manner to give 3-p-biphenylyl-butylamine. Hydrochloride, m.p. 226°-228°.

The following can be obtained analogously from the corresponding amides:
2-p-Biphenylyl-propylamine, 2-(4'-fluoro-4-biphenylyl)-propylamine, dl-malate, m.p. 157°–159°,
2-(4'-chloro-4-biphenylyl)-propylamine,
2-(4'-p-chlorophenoxy-phenyl)-propylamine,
3-(2-fluoro-4-biphenylyl)-butylamine,
3-(3-fluoro-4-biphenylyl)-butylamine,
3-(2'-fluoro-4-biphenylyl)-butylamine, dl-malate, m.p. 156°–158°,
3-(3'-fluoro-4-biphenylyl)-butylamine,
3-(4'-fluoro-4-biphenylyl)-butylamine, hydrochloride, m.p. 222°–224°,
3-(2-chloro-4-biphenylyl)-butylamine,
3-(3-chloro-4-biphenylyl)-butylamine,
3-(2'-chloro-4-biphenylyl)-butylamine,
3-(3'-chloro-4-biphenylyl)-butylamine,
3-(4'-chloro-4-biphenylyl)-butylamine, tartrate, m.p. 200°–202°, hydrochloride, m.p. 256 - 259°.
3-(2-bromo-4-biphenylyl)-butylamine,
3-(3-bromo-4-biphenylyl)-butylamine,
3-(2'-bromo-4-biphenylyl)-butylamine,
3-(3'-bromo-4-biphenylyl)-butylamine,
3-(4'-bromo-4-biphenylyl)-butylamine,
3-(2',4-difluoro-4-biphenylyl)-butylamine, dl-malate, m.p. 152-154°,
3-(2',4'-dichloro-4-biphenylyl)-butylamine,
3-(2',4'-dibromo-4-biphenylyl)-butylamine,
3-(2+,4'-dibromo-4-biphenylyl)-butylamine,
3-(2'-fluoro-4'-chloro-4-biphenylyl)-butylamine,
3-(2'-fluoro-4'-bromo-4-biphenylyl)-butylamine,
3-(2'-chloro-4'-fluoro-4-biphenylyl)-butylamine,
3-(2'-bromo-4'-fluoro-4-biphenylyl)-butylamine,
3-p-phenoxyphenyl-butylamine,
3-(4-o-fluorophenoxy-phenyl)-butylamine,
3-(4-p-fluorophenoxy-phenyl)-butylamine,
3-(4-o-chlorophenoxy-phenyl)-butylamine,
3-(4-p-chlorophenoxy-phenyl)-butylamine, hydrochloride, m.p. 125°–127°,
3-(4-o-bromophenoxy-phenyl)-butylamine,
3-(4-p-bromophenoxy-phenyl)-butylamine,
3-[4-(2,4-difluorophenoxy)-phenyl]-butylamine,
3-[4-(2,4-dichlorophenoxy)-phenyl]-butylamine,
3-[4-(2,4-dibromophenoxy)-phenyl]-butylamine,
4-p-biphenylyl-pentylamine,
4-(4'-fluoro-4-biphenylyl)-pentylamine, dl-malate, m.p. 159°–161°,
4-(4'-chloro-4-biphenylyl)-pentylamine and
4-(4-p-chlorophenoxy-phenyl)-pentylamine.

EXAMPLE 2

3-p-Biphenylyl-3-hydroxy-butylamine, hydrochloride, m.p. 272°–275°, is obtained analogously to Example 1, using LiAlH$_4$, from 3-p-biphenylyl-3-hydroxybutyramide (which can be prepared from the corresponding ethyl ester (m.p. 55°–56°) and NH$_3$).

The following can be obtained from the corresponding hydroxyamides:
2-p-Biphenylyl-2-hydroxy-propylamine,
2-(4'-fluoro-4-biphenylyl)-2-hydroxy-propylamine,
2-(4'-chloro-4-biphenylyl)-2-hydroxy-propylamine,
2-(4-p-chlorophenoxy-phenyl)-2-hydroxy-propylamine,
3-(2-fluoro-4-biphenylyl)-3-hydroxy-butylamine,
3-(3-fluoro-4-biphenylyl)-3-hydroxy-butylamine,
3-(2'-fluoro-4-biphenylyl)3-hydroxy-butylamine, hydrochloride, m.p. 200° - 202°,
3-(3'-fluoro-4-biphenylyl)-3-hydroxy-butylamine,
3-(4'-fluoro-4-biphenylyl)-3-hydroxy-butylamine, m.p. 144°–146°.
3-(2-chloro-4-biphenylyl)-3-hydroxy-butylamine,
3-(3-chloro-4-biphenylyl)-3-hydroxy-butylamine,
3-(2'-chloro-4-biphenylyl)-3-hydroxy-butylamine,
3-(3'-chloro-4-biphenylyl)-3-hydroxy-butylamine,
3-(4'-chloro-4-biphenylyl)-3-hydroxy-butylamine, hydrochloride, m.p. 290° - 293°; tartrate, m.p. 191° - 194° (decomposition),
3-(2-bromo-4-biphenylyl)-3-hydroxy-butylamine,
3-(3-bromo-4-biphenylyl)-3-hydroxy-butylamine,
3-(2'-bromo-4-biphenylyl)-3-hydroxy-butylamine,
3-(3'-bromo-4-biphenylyl)-3-hydroxy-butylamine,
3-(4'-bromo-4-biphenylyl)-3-hydroxy-butylamine,
3-(2',4'-difluoro-4-biphenylyl)-3-hydroxy-butylamine,
3-(2',4'-dichloro-4-biphenylyl)-3-hydroxy-butylamine,
3-(2',4'-difluoro-4-biphenylyl)-3-hydroxy-butylamine,
3-(2'-fluoro-4'-chloro-4-biphenylyl)-3-hydroxy-butylamine,
3-(2'-fluoro-4'-bromo-4-biphenylyl)-3-hydroxy-butylamine,
3-(2'-chloro-4'-fluoro-4-biphenylyl)-3-hydroxy-butylamine,
3-(2'-bromo-4'-fluoro-4-biphenylyl)-3-hydroxy-butylamine,
3-p-phenoxyphenyl-3-hydroxy-butylamine,
3-(4-o-fluorophenoxy-phenyl)-3-hydroxy-butylamine,
3-(4-p-fluorophenoxy-phenyl)-3-hydroxy-butylamine,
3-(4-o-chlorophenoxy-phenyl)-3-hydroxy-butylamine,
3-(4-p-chlorophenoxy-phenyl)-3-hydroxy-butylamine, m.p. 96°–98°,
3-(4-o-bromophenoxy-phenyl)-3-hydroxy-butylamine,
3-(4-p-bromophenoxy-phenyl)-3-hydroxy-butylamine,
3-[4-(2,4-difluorophenoxy)-phenyl]-3-hydroxy-butylamine,
3-[4-(2,4-dichlorophenoxy)-phenyl]-3-hydroxy-butylamine,
3-[4-(2,4-dibromophenoxy)-phenyl]-3-hydroxy-butylamine, DL-malate, m.p. 88° (with decomposition)
4-p-biphenylyl-4-hydroxy-pentylamine,
4-(4'-fluoro-4-biphenylyl)-4-hydroxy-pentylamine,
4-(4'-chloro-4-biphenylyl)-4-hydroxy-pentylamine and
4-(4-p-chlorophenoxy-phenyl)-4-hydroxy-pentylamine.

EXAMPLE 3

A solution of 2.37 g of 3-p-biphenylyl-2-butenoic acid amide (which can be prepared from the corresponding 3-hydroxy-butyramide and p-toluenesulphonic acid in toluene) in 30 ml of benzene is added dropwise, while stirring, to a suspension of 5 g of sodium aluminium bis-(2-methoxyethoxy)dihydride in 30 ml of benzene. The mixture is boiled overnight, cooled and carefully decomposed by means of water, and worked up in the customary manner to give 3-p-biphenylyl-2-butenyl-1-amine.

The following are obtained analogously from the corresponding butenoic acid amides:
3-(2-Fluoro-4-biphenylyl)-2-butenyl-1-amine,
3-(3-fluoro-4-biphenylyl)-2-butenyl-1-amine,
3-(2'-fluoro-4-biphenylyl)-2-butenyl-1-amine,
3-(3'-fluoro-4-biphenylyl)-2-butenyl-1-amine,
3-(4'-fluoro-4-biphenylyl)-2-butenyl-1-amine,
3-(2-chloro-4-biphenylyl)-2-butenyl-1-amine,
3-(3-chloro-4-biphenylyl)-2-butenyl-1-amine,
3-(2'-chloro-4-biphenylyl)-2-butenyl-1-amine,
3-(3'-chloro-4-biphenylyl)-2-butenyl-1-amine,
3-(4'-chloro-4-biphenylyl)-2-butenyl-1-amine,
3-(2-bromo-4-biphenylyl)-2-butenyl-1-amine,
3-(3-bromo-4-biphenylyl)-2-butenyl-1-amine,
3-(2'-bromo-4-biphenylyl)-2-butenyl-1-amine, 3-(3'-bromo-4-biphenylyl)-2-butenyl-1-amine,
3-(4'-bromo-4-biphenylyl)-2-butenyl-1-amine,
3-(2',4'-difluoro-4-biphenylyl)-2-butenyl-1-amine,
3-(2',4'-dichloro-4-biphenylyl)-2-butenyl-1-amine,
3-(2',4'-dibromo-4-biphenylyl)-2-butenyl-1-amine,
3-(2'-fluoro-4'-chloro-4-biphenylyl)-2-butenyl-1-amine,
3-(2'-fluoro-4'-bromo-4-biphenylyl)-2-butenyl-1-amine,
3-(2'-chloro-4'-fluoro-4-biphenylyl)-2-butenyl-1-amine,
3-(2'-bromo-4'-fluoro-4-biphenylyl)-2-butenyl-1-amine,
3-p-phenoxyphenyl-2-butenyl-1-amine,
3-(4-o-fluorophenoxy-phenyl)-2-butenyl-1-amine,
3-(4-p-fluorophenoxy-phenyl)-2-butenyl-1-amine,
3-(4-o-chlorophenoxy-phenyl)-2-butenyl-1-amine,
3-(4-p-chlorophenoxy-phenyl)-2-butenyl-1-amine,
3-(4-o-bromophenoxy-phenyl)-2-butenyl-1-amine,
3-(4-p-bromophenoxy-phenyl)-2-butenyl-1-amine,
3-[4-(2,4-difluorophenoxy)-phenyl]-2-butenyl-1-amine,
3-[4-(2,4-dichlorophenoxy)-phenyl]-2-butenyl-1-amine
and
3-[4-(2,4-dibromophenoxy)-phenyl]-2-butenyl-1-amine.

EXAMPLE 4

A solution of 27.5 g of 3-(4'-chloro-4-biphenylyl)-butyramide [m.p. 185° – 187°; obtainable from p-chlorobiphenyl via 4-acetyl-4'-chlorobiphenyl (m.p. 100° – 103°), 3-(4'-chloro-4-biphenylyl)-3-hydroxybutyric acid ethyl ester (m.p. 72°–74°) and 3-(4'-chloro-4-biphenylyl)-butyric acid (m.p. 154°–156°)] in 300 ml of THF is added dropwise, while stirring, to a solution of 4.6 g of diborane in 50 ml of THF, and the mixture is boiled for two hours, cooled and treated with 25% hydrochloric acid. It is then poured into water and worked up with sodium hydroxide solution and ethyl acetate to give 3-(4'-chloro-4-biphenylyl)-butylamine. Hydrochloride, m.p. 256°–259°.

EXAMPLE 5

A solution of 23.9 g of 3-(4'-fluoro-4-biphenylyl)-butyronitrile (obtainable from the amide employing p-toluenesulphonyl chloride/pyridine) in 250 ml of methanol is hydrogenated for 3 hours at about 80 ats. and 80°, after adding 8 g of KOH and 12 g of Raney nickel, and the mixture is filtered, evaporated and worked up with water and dichloromethane. After drying and evaporating the organic phase, 3-(4'-fluoro-4-biphenylyl)-butylamine, hydrochloride, m.p. 222°–224°, is obtained.

EXAMPLE 6

A solution of 80 g of $Na_2S_2O_4$ in 350 ml of water is added to a solution of 27.3 g of 1-nitro-3-(4'-fluoro-4-biphenylyl)-butane [obtainable by reduction of 3-(4'-fluoro-4-biphenylyl)-butyric acid, using $LiAlH_4$, to give the alcohol, reaction with $PBr_3$ to give 1-bromo-3-(4'-fluoro-4-biphenylyl)butane and reaction with $NaNO_2$] in 500 ml of hot ethanol. The mixture is boiled for an hour and filtered and the solution is concentrated and worked up with aqueous sodium hydroxide solution and chloroform to give 3-(4'-fluoro-4-biphenylyl)-butylamine. Hydrochloride, m.p. 222°–224°.

EXAMPLE 7

A mixture of 24.2 g of 3-(4'-fluoro-4-biphenylyl)butanal [obtainable by oxidation of 3-(4'-fluoro-4-biphenylyl)-butanol with $CrO_3$], 40 g of liquid ammonia and 400 ml of methanol is heated at 100° for 12 hours. In the course thereof, 1-hydroxy-3-(4'-fluoro-4-biphenylyl)butylamine and 3-(4'-fluoro-4-biphenylyl)-butylidene-imine, which are not isolated, are probably formed as intermediate products. 30 g of Raney nickel are then added and the mixture is hydrogenated for about 20 hours at 100 m and 100°, and is filtered and evaporated to give 3-(4'-fluoro-4-biphenylyl)-butylamine. Hydrochloride, m.p. 222°–224°.

EXAMPLE 8

25.7 g of 3-(4'-fluoro-4-biphenylyl)-butanaldoxime (obtainable from the aldehyde and hydroxylamine) are dissolved in 500 ml of ethanol and hydrogenated over 3 g of $PtO_2$ at 20° and normal pressure until hydrogen absorption ceases, and the mixture is filtered and evaporated to give 3-(4'-fluoro-4-biphenylyl)-butylamine. Hydrochloride, m.p. 222°–224°.

EXAMPLE 9

23.7 g of 3-(4'-fluorobiphenylyl)-2-butenoic acid nitrile (obtainable from 4-acetyl-4'-fluorobiphenyl and cyanoacetic acid) are dissolved in 150 ml of isopropanol, 15 g of liquid $NH_3$ and 3 g of Raney Ni, moist with isopropanol, are added and the mixture is hydrogenated for 4 hours at 80° and 80 ats. After filtration and evaporation, 3-(4'-fluoro-4-biphenylyl)-butylamine is obtained. Hydrochloride, m.p. 222°–224°.

EXAMPLE 10

A solution of 33.3 g of N-benzyl-3-(4'-fluoro-4-biphenylyl)-1-butylamine [obtainable by reacting 3-(4'-fluoro-4-biphenylyl)-butanol with $SOCl_2$] to give 1-chloro-3-(4'-fluoro-4-biphenylyl)-butane and reaction with benzylamine in 500 ml of methanol is hydrogenated over 8 g of 5% Pd-on-charcoal at 20° and normal pressure. After filtration and evaporation, 3-(4'-fluoro-4-biphenylyl)-butylamine is obtained. Hydrochloride, m.p. 222°–224°.

The same product can be obtained analogously from N-benzylidene-3-(4'-fluoro-4-biphenylyl)-1-butylamine or from N,N-dibenzyl-3-(4'-fluoro-4-biphenylyl)-1-butylamine.

EXAMPLE 11

A solution of 2.79 g of 1-isobutylideneamino-3-p-biphenylyl-butane (obtainable by boiling 3-p-biphenylylbutylamine with isobutyraldehyde in benzene for 5 hours) in 75 ml of methanol is hydrogenated, after adding 0.3 g of $PtO_2$, at 20° and normal pressure until hydrogen absorption ceases. The mixture is filtered and worked up in the customary manner to give 1-isobutylamino-3-p-biphenylyl-butane.

EXAMPLE 12

A solution of 2.65 g of 1-isopropylimino-3-p-biphenylyl-butane (obtainable from 3-p-biphenylyl-butanal and isopropylamine) in 25 ml of dioxane is hydrogenated, over 0.2 g of platinum, at 20° and normal pressure until hydrogen absorption ceases. The mixture is filtered and evaporated to give 1-isopropylamino-3-p-biphenylyl-butane.

EXAMPLE 13

A solution of 2.22 g of 3-p-biphenylyl-2-buten-1-al (obtainable by reacting 4-acetylbiphenyl with 2,2-diethoxy-ethylmagnesium bromide and subsequent treatment with p-toluenesulfonic acid) and 0.6 g of isopropylamine in 25 ml of methanol is heated at 200° for 5 hours in a tube. After cooling, 0.5 g of Raney nickel, moist with methanol, is added and the resulting Schiff's base is hydrogenated for one hour at 100 atms. and 80°. The mixture is cooled and filtered and 1-isopropylamino-3-p-biphenylyl-butane is obtained.

EXAMPLE 14

A solution of 2.63 g of 1-isopropylimino-3-p-biphenylyl-2-butene (obtainable from 3-p-biphenylyl-2-butenal and isopropylamine) in 20 ml of absolute ether is added dropwise to a solution of 0.6 g of LiAlH$_4$ in 20 ml of absolute ether. The mixture is then boiled for 5 hours, water is added carefully and the mixture is worked up in the customary manner to give 1-isopropylamino-3-p-biphenylyl-2-butene.

EXAMPLE 15

A solution of 2.77 g of 1-pyrrolidino-3-p-biphenylyl-1-butene (obtainable from 3-p-biphenylyl-butanal and pyrrolidine) in 35 ml of ethanol is hydrogenated, over 0.5 g of Raney nickel, for 3 hours at 6 atms and 60°. The catalyst is filtered off and the solution is evaporated to give 1-pyrrolidino-3-p-biphenylyl-butane.

EXAMPLE 16

1.5 g of zinc dust are added, while stirring, to a solution of 2.39 g of 3-p-biphenylyl-butanaldoxime in 25 ml of acetic acid. The mixture is stirred for a further 4 hours, filtered, diluted with water, rendered alkaline with ammonia and extracted with chloroform. After the customary working up, 3-p-biphenylyl-butylamine is obtained. Hydrochloride, m.p. 226°–228°.

EXAMPLE 17

The following are obtained analogously to Example 1, using LiAlH$_4$, from the corresponding diethylamides, morpholides or piperidides:
1-Diethylamino-3-(4'-chloro-4-biphenylyl)-butane, m.p. 42°–44°,
1-piperidino-3-p-biphenylyl-butan-3-ol, m.p. 102°–104°,
1-piperidino-3-(4'-fluoro-4-biphenylyl)-butan-3-ol, m.p. 107°–109°,
1-piperidino-3-(4'-bromo-4-biphenylyl)-butan-3-ol, m.p. 89°–91°.
1-piperidino-3-(4-p-chlorophenoxy-phenyl)-butan-3-ol, m.p. 73°–74°,
1-piperidino-3-(4-p-bromophenoxy-phenyl)-butan-3-ol, m.p. 73°–75°,
1-morpholino-3-p-biphenylyl-butan-3-ol, m.p. 116°–118°,
1-morpholino-3-(4'-fluoro-4-biphenylyl)-butan-3-ol, m.p. 152°–154°,
1-morpholino-3-(4'-chloro-4-biphenylyl)-butan-3-ol, m.p. 106°–108°,
1-morpholino-3-(4'-bromo-4-biphenylyl)-butan-3-ol, m.p. 97°–99° and
1-morpholino-3-(4-p-chlorophenoxy-phenyl)-butan-3ol, m.p. 66°–67°.

EXAMPLE 18

1-piperidino-3-p-biphenylyl-butan-3-ol, m.p. 102°–104°, is obtained analogously to Example 1, using LiAlH$_4$, from 1-(2-oxo-piperidino)-3-p-biphenylyl-butan-3-ol (obtainable from 3-p-biphenylyl-3-hydroxy-butylamine and 5-bromovaleryl bromide).

EXAMPLE 19

A mixture of 3.23 g of 1-(4-oxopiperidino)-3-p-biphenylyl-butan-3-ol (obtainable from 1-chloro-3-p-biphenylyl-butan-3-ol and 4-piperidone), 1.5 g of KOH, 2.5 ml of 85% hydrazine and 25 ml of diethylene glycol is warmed at 100° for 1 hour. The temperature is raised slowly until the hydrazone is decomposed, and the mixture is boiled for a further 4 hours, cooled and worked up in the customary manner to give 1-piperidino-3-p-biphenylyl-butan-3-ol, m.p. 102° – 104°.

EXAMPLE 20

4.05 g of 1-dibenzylamino-3p-biphenylyl-butane (obtainable by reacting 1-chloro-3-p-biphenylyl-butan-3-ol with dibenzylamine to give 1-dibenzylamino-3p-biphenylyl-butan-3-ol and subsequent reduction with HI) is dissolved in 50 ml of ethyl acetate and hydrogenated, over 0.5 g. of 10% Pd-on-charcoal, at 20° and 1 at. until hydrogen absorption ceases. The mixture is filtered and evaporated to give 3-p-biphenylyl-butylamine. Hydrochloride, m.p. 226° – 228°.

EXAMPLE 21

A solution of 27.1 g of 4-(4'-fluoro-4-biphenylyl)-pentanoic acid amide [obtainable by reacting 4-fluorobiphenyl with succinic anhydride/AlCl$_3$ to give 4-(4'-fluoro-4-biphenylyl)-4-oxobutanoic acid, reaction with CH$_3$MgI to give 4-(4'-fluoro-4-biphenylyl)-4-hydroxy-pentanoic acid, dehydroxylation with HI/acetic acid to give 4-(4'-fluoro-4-biphenylyl)-pentanoic acid, conversion into the chloride employing SOCl$_2$ and reaction with NH$_3$] in 150 ml of dioxane is added dropwise at 0° to a solution of 24 g of bromine in 120 ml of 20% potassium hydroxide solution. The mixture is stirred for a further 1 hour, taken up in ether, the phases are separated and the organic phase is dried over sodium sulfate and evaporated. The crude product obtained is boiled for 20 hours with 60 g of KOH, 250 ml of methanol and 65 ml of water, in the course of which 3-(4'-fluoro-4-biphenylyl)-butyl-isocyanate, which is not isolated, is formed. After cooling, the mixture is worked up using water and ether to give 3-(4'-fluoro-4-biphenylyl)-butylamine, hydrochloride; m.p. 222°–224°.

EXAMPLE 22

A solution of 24.4 g of 1-amino-3-(4'-fluoro-4-biphenylyl)-propan-3-one [obtainable by reacting 1-chloro-3-(4'-fluoro-4-biphenylyl)-propan-3-one with potassium phthalimide and subsequent hydrolysis] in 200 ml of THF is added dropwise, while stirring, at 20° to a Grignard solution prepared from 30 g of CH$_3$I and 5 g of magnesium in 1000 ml of ether. The mixture is stirred for a further 4 hours, the resulting alcoholate is decomposed by means of water and dilute sulfuric acid, and the mixture is worked up in the customary manner to give 3-(4-fluoro-4-biphenylyl)-3-hydroxybutylamine, m.p. 144° – 146°.

1-Morpholino-3-(4'-chloro-4-biphenylyl)-butan-3-ol, m.p. 106° – 108°, is obtained analogously by hydrolysis of the alcoholate prepared from 1-morpholino-3-(4'-chloro-4-biphenylyl)-propan-3-one (obtainable from 4-p-chlorophenylacetophenone, morpholine and formaldehyde) and CH$_3$MgI.

EXAMPLE 23

4.35 g of 1-aminobutan-3-one in 400 ml of ether are added dropwise, while stirring, at 20° to a Grignard solution formed from 25.1 g of 4'-fluoro-4-bromo-biphenyl (obtainable by brominating 4-fluoro-biphenyl) and 2.43 g of magnesium in 1,000 ml of ether, the mixture is stirred for a further two hours, the resulting alcoholate is decomposed employing dilute sulfuric acid, and the mixture is worked up in the customary manner to give 3-(4'-fluoro-4-biphenylyl)-3-hydroxybutylamine, m.p. 144° – 146°.

EXAMPLE 24

3.59 g of 3-bromo-3-(4'-fluoro-4-biphenylyl)butylamine hydrochloride [obtainable by reacting 3-hydroxy-3-(4'-fluoro-4-biphenylyl)-butyramide with PBr$_3$ to give 3-bromo-3-(4'-fluoro-4-biphenylyl)-butyramide and reduction with LiAlH$_4$] are dissolved in a mixture of 15 ml of acetone and 15 ml of water, 1 drop of sulfuric acid is added, and the mixture is warmed to 45° for 4 hours and worked up in the customary manner to give 3-(4'-fluoro-4-biphenylyl)-3-hydroxybutylamine, m.p. 144° – 146°. A little 3-(4'-fluoro-4-biphenylyl)-2-butenylamine, which can be removed by chromatography (over SiO$_2$), is formed as a by-product.

EXAMPLE 25

30.1 g of 3-acetoxy-3-(4'-fluoro-4-biphenylyl)-1-butylamine [obtainable from 3-bromo-3-(4'-fluoro-4-biphenylyl)-1-butylamine and potassium acetate] are boiled for 2 hours with 20 g of KOH in 500 ml of methanol, and the mixture is worked up with water and chloroform to give 3-(4'-fluoro-4-biphenylyl)-3-hydroxybutylamine, m.p. 144° – 146°.

EXAMPLE 26

24.2 g of 3-(4'-fluoro-4-biphenylyl)-1-buten-3-ol (obtainable from 4-acetyl-4'-fluorobiphenyl and vinylmagnesium bromide) are heated with 8 g of ammonia and 0.25 g of sodium for 8 hours at 180° – 200°, and the mixture is cooled and worked up with water and chloroform to give 3-(4'-fluoro-4-biphenylyl)-3-hydroxybutylamine, m.p. 144° – 146°.

3-(4'-Fluoro-4-biphenylyl)-butylamine, hydrochloride, m.p. 222° – 224°, is obtained analogously from 3-(4'-fluoro-4-biphenylyl)-1-butene.

EXAMPLE 27

A solution of 26.25 g of 1-chloro-3-(4'-fluoro-4-biphenylyl)-butane [obtainable by a Friedel-Crafts reaction of 4-fluoro-biphenyl with 3-chloropropionyl chloride to give 4'-fluoro-4-(3-chloropropionyl)-biphenyl (m.p. 96° – 97°), reaction with CH$_3$MgI to give 1-chloro-3-(4'-fluoro-4-biphenylyl)-butan-3-ol (m.p. 78° – 79°) and reduction using HI] in 150 ml of absolute ethanol is added dropwise at 0° to a solution of 10 g of NH$_3$ in 150 ml of absolute ethanol. The solution is stirred for a further 2 hours at 20°, concentrated and worked up with aqueous sodium hydroxide solution and ether to give 3-(4'-fluoro-4-biphenylyl)-butylamine; hydrochloride, m.p. 222° – 224°.

EXAMPLE 28

A solution of 2.6 g of 1-chloro-3-p-biphenylylbutan-3-ol [m.p. 68° – 70°; obtainable by a Friedel-Crafts reaction of biphenyl with 3-chloropropionyl chloride to give 4-(3-chloropropionyl)-biphenyl and reaction with CH$_3$MgI; or 3.05 g of 1-bromo-3-p-biphenylyl-butan-3-ol or 3.96 g of 1-p-toluenesulfonyloxy-3-p-biphenylyl-butan-3-ol] and 30g of methylamine in 100 ml of methanol is heated at 120° for 2 hours in an autoclave. After cooling and working up in the customary manner, 1-methylamino-3-p-biphenylyl-butan-3-ol is obtained.

The following are obtained analogously from the corresponding chlorine or bromine compounds:
1-Methylamino-3-(4'-fluoro-4-biphenylyl)-butan-3-ol,
1-methylamino-3-(4'-chloro-4-biphenylyl)-butan-3-ol,
1-methylamino-3-(4-p-chlorophenoxy-phenyl)-butan-3-ol,
1-ethylamino-3-p-biphenylyl-butan-3-ol,
1-ethylamino-3-(4'-fluoro-4-biphenylyl)-butan-3-ol,
1-ethylamino-3-(4'-chloro-4-biphenylyl)-butan-3-ol,
1-ethylamino-3-(4-p-chlorophenoxy-phenyl)-butan-3-ol,
1-n-propylamino-3-p-biphenylyl-butan-3-ol,
1-n-propylamino-3-(4'-fluoro-4-biphenylyl)-butan-3-ol,
1-n-propylamino-3-(4'-chloro-4-biphenylyl)-butan-3-ol,
1-n-propylamino-3-(4-p-chlorophenoxy-phenyl)-butan-3-ol,
1-isopropylamino-3-p-biphenylyl-butan-3-ol,
1-isopropylamino-3-(4'-fluoro-4-biphenylyl)-butan-3-ol,
1-isopropylamino-3-(4'-chloro-4-biphenylyl)-butan-3-ol,
1-isopropylamino-3-(4-p-chlorophenoxy-phenyl)-butan-3-ol,
1-n-butylamino-3-p-biphenylyl-butan-3-ol,
1-n-butylamino-3-(4'-fluoro-4-biphenylyl)-butan-3-ol,
1-n-butylamino-3-(4'-chloro-4-biphenylyl)-butan-3-ol,
1-n-butylamino-3-(4-p-chlorophenoxy-phenyl)-butan-3-ol,
1-isobutylamino-3-p-biphenylyl-butan-3-ol,
1-isobutylamino-3-(4'-fluoro-4-biphenylyl)-butan-3-ol,
1-isobutylamino-3-(4'-chloro-4-biphenylyl)-butan-3-ol,
1-isobutylamino-3-(4-p-chlorophenoxy-phenyl)-butan-3-ol,
1-sec.-butylamino-3-p-biphenylyl-butan-3-ol,
1-sec.-butylamino-3-(4'-fluoro-4-biphenylyl)-butan-3-ol,
1-sec.-butylamino-3-(4'-chloro-4-biphenylyl)-butan-3-ol,
1-sec.-butylamino-3-(4-p-chlorophenoxy-phenyl)-butan-3-ol,
1-tert.-butylamino-3-p-biphenylyl-butan-3-ol,
1-tert.-butylamino-3-(4'-fluoro-4-biphenylyl)-butan-3-ol,
1-tert.-butylamino-3-(4'-chloro-4-biphenylyl)-butan-3-ol,
1-tert.-butylamino-3-(4-p-chlorophenoxy-phenyl)-butan-3-ol,
1-n-pentylamino-3-p-biphenylyl-butan-3-ol and
1-n-hexylamino-3-p-biphenylyl-butan-3-ol.

EXAMPLE 29

2.6 g of 1-chloro-3-p-biphenylyl-butan-3-ol are boiled with 30 ml of morpholine for 1.5 hours and the mixture is cooled and worked up in the customary manner to give 1-morpholino-3-p-biphenylyl-butan-3-ol, m.p. 116° –118°.

The following are obtained analogously from the corresponding chlorine or bromine compounds:
1-Morpholino-2-p-biphenylyl-propan-2-ol,
1-morpholino-2-(4'-fluoro-4-biphenylyl)-propan-2-ol,
1-morpholino-2-(4'-chloro-4-biphenylyl)-propan-2-ol,
1-morpholino-2-(4'-bromo-4-biphenylyl)-propan-2-ol,
1-morpholino-2-(4-p-chlorophenoxy-phenyl)-propan-2-ol,
1-morpholino-3-(2'-fluro-4-biphenylyl)-butan-3-ol,
1-morpholino-3-(4'-fluoro-4-biphenylyl)-butan-3-ol, m.p. 152° – 154°,
1-morpholino-3-(2'-chloro-4-biphenylyl)-butan-3-ol,
1-morpholino-3-(4'-chloro-4-biphenylyl)-butan-3-ol, m.p. 106° –108°,
1-morpholino-3-(2'-bromo-4-biphenylyl)-butan-3-ol,
1-morpholino-3-(4'-bromo-4-biphenylyl)-butan-3-ol, m.p. 97° –99°, 1-morpholino-3-(2',4'-difluoro-4-biphenylyl)-butan-3-ol,
1-morpholino-3-(2',4'-dichloro-4-biphenylyl)-butan-3-ol,
1-morpholino-3-(2',4'-dibromo-4-biphenylyl)-butan-3-ol,
1-morpholino-3-p-phenoxy-phenyl-butan-3-ol,
1-morpholino-3-(4-o-fluorophenoxy-phenyl)-butan-3-ol,
1-morpholino-3-(4-p-fluorophenoxy-phenyl)-butan-3-ol,
1-morpholino-3-(4-o-chlorophenoxy-phenyl)-butan-3-ol,
1-morpholino-3-(4-p-chlorophenoxy-phenyl)-butan-3-ol, m.p. 66° – 67°,
1-morpholino-3-(4-o-bromophenoxy-phenyl)-butan-3-ol,
1-morpholino-3-(4-p-bromophenoxy-phenyl)-butan-3-ol,
1-morpholino-3-[4-(2,4-difluorophenoxy)-phenyl]-butan-3-ol,
1-morpholino-3-[4-(2,4-dichlorophenoxy)-phenyl]-butan-3-ol,
1-morpholino-3-[4-(2,4-dibromophenoxy)-phenyl]-butan-3-ol,
1-morpholino-4-p-biphenylyl-pentan-4-ol,
1-morpholino-4-(4'-fluoro-4-biphenylyl)-pentan-4-ol,
1-morpholino-4-(4'-chloro-4-biphenylyl)-pentan-4-ol,
1-morpholino-4-(4'-bromo-4-biphenylyl)-pentan-4-ol and
1-morpholino-4-(4-p-chlorophenoxy-phenyl)-pentan-4-ol.

EXAMPLE 30

The following are obtained, analogously to Example 29, from the corresponding chlorine or bromine compounds, using pyrrolidine, piperidine, 4-methylpiperidine, homopiperidine or piperazine:
1-Pyrrolidino-3-p-biphenylyl-butan-3-ol,
1-pyrrolidino-3-(2'-fluoro-4-biphenylyl)-butan-3-ol,
1-pyrrolidino-3-(4'-fluoro-4-biphenylyl)-butan-3-ol,
1-pyrrolidino-3-(2'-chloro-4-biphenylyl)-butan-3-ol,
1-pyrrolidino-3-(4'-chloro-4-biphenylyl)-butan-3-ol,
1-pyrrolidino-3-(2'-bromo-4-biphenylyl)-butan-3-ol,
1-pyrrolidino-3-(4'-bromo-4-biphenylyl)-butan-3-ol,
1-pyrrolidino-3-(2',4'-difluoro-4-biphenylyl)-butan-3-ol,
1-pyrrolidino-3-(2',4'-dichloro-4-biphenylyl)-butan-3-ol,
1-pyrrolidino-3-(2',4'-dibromo-4-biphenylyl)-butan-3-ol,
1-pyrrolidino-3-p-phenoxy-phenyl-butan-3-ol,
1-pyrrolidino-3-(4-o-fluorophenoxy-phenyl)-butan-3-ol,
1-pyrrolidino-3-(4-p-fluorophenoxy-phenyl)-butan-3-ol,
1-pyrrolidino-3-(4-o-chlorophenoxy-phenyl)-butan-3-ol,
1-pyrrolidino-3-(4-p-chlorophenoxy-phenyl)-butan-3-ol,
1-pyrrolidino-3-(4-o-bromophenoxy-phenyl)-butan-3-ol,
1-pyrrolidino-3-(4-p-bromophenoxy-phenyl)-butan-3-ol,
1-pyrrolidino-3-[4-(2,4-difluorophenoxy)-phenyl]-butan-3-ol,
1-pyrrolidino-3-[4-(2,4-dichlorophenoxy)-phenyl]-butan-3-ol,
1-pyrrolidino-3-[4-(2,4-dibromophenoxy)-phenyl]-butan-3-ol,
1-piperidino-2-p-biphenylyl-propan-2-ol,
1-piperidino-2-(4'-fluoro-4-biphenylyl)-propan-2-ol,
1-piperidino-2-(4'-chloro-4-biphenylyl)-propan-2-ol,
1-piperidino-2-(4'-bromo-4-biphenylyl)-propan-2-ol, hydrochloride, m.p. 245° – 247°,
1-piperidino-2-(4-p-chlorophenoxy-phenyl)-propan-2-ol,
1-piperidino-3-p-biphenylyl-butan-3-ol, m.p. 102° – 104°,
1-piperidino-3-(2'-fluoro-4-biphenylyl)-butan-3-ol,
1-piperidino-3-(4'-fluoro-4-biphenylyl)-butan-3-ol, m.p. 107°–109°, hydrochloride, m.p. 238°–242°,
1-piperidino-3-(2'-chloro-4-biphenylyl)-butan-3-ol,
1-piperidino-3-(4'-chloro-4-biphenylyl)-butan-3-ol, m.p. 90°–91°,
1-piperidino-3-(2'-bromo-4-biphenylyl)-butan-3-ol,
1-piperidino-3-(4'-bromo-4-biphenylyl)-butan-3-ol, m.p. 89°–91°,
1-piperidino-3-(2',4'-difluoro-4-biphenylyl)-butan-3-ol,
1-piperidino-3-(2',4'-dichloro-4-biphenylyl)-butan-3-ol,
1-piperidino-3-(2',4'-dibromo-4-biphenylyl)-butan-3-ol,
1-piperidino-3-p-phenoxy-phenyl-butan-3ol,
1-piperidino-3-(4-o-fluorophenoxy-phenyl)-butan-3-ol,
1-piperidino-3-(4-p-fluorophenoxy-phenyl)-butan-3-ol, m.p. 50°–51°,
1-piperidino-3-(4-o-chlorophenoxy-phenyl)-butan-3-ol,
1-piperidino-3-(4-o-chlorophenoxy-phenyl)-butan-3-ol, m.p. 73°–75°,
1-piperidino-3-(4-o-bromophenoxy-phenyl)-butan-3-ol,
1-piperidino-3-(4-p-bromophenoxy-phenyl)-butan-3-ol, m.p. 73°–75°,
1-piperidino-3-[4-(2,4-difluorophenoxy)-phenyl]-butan-3-ol,
1-piperidino-3-[4-(2,4-dichlorophenoxy)-phenyl]-butan-3-ol,
1-priperidino-3-[4-(2,4-dibromophenoxy)-phenyl]-butan-3-ol,
1-piperidino-4-p-biphenylyl-pentan-4-ol,
1-piperidino-4-(4'-fluoro-4-biphenylyl)-pentan-4-ol,
1-piperidino-4-(4'-chloro-4-biphenylyl)-pentan-4-ol,
1-piperidino-4-(4'-bromo-4-biphenylyl)-pentan-4-ol, hydrochloride, m.p. 282° –283°,
1-piperidino-4-(4-p-chlorophenoxy-phenyl)-pentan-4-ol,
1-(4-methylpiperidino)-3-p-biphenylyl-butan-3-ol,
1-(4-methylpiperidino)-3-(2'-fluoro-4-biphenylyl)-butan-3-ol,
1-(4-methylpiperidino)-3-(4'-fluoro-4-biphenylyl)-butan-3-ol, hydrochloride, m.p. 222°,
1-(4-methylpiperidino)-3-(2'-chloro-4-biphenylyl)-butan-3-ol,
1-(4-methylpiperidino)-3-(4'-chloro-4-biphenylyl)-butan-3-ol,
1-(4-methylpiperidino)-3-(2'-bromo-4-biphenylyl)-butan-3-ol,
1-(4-methylpiperidino)-3-(4'-bromo-4-biphenylyl)-butan-3-ol,
1-(4-methylpiperidino)-3-(2',4'-difluoro-4-biphenylyl)-butan-3-ol,
1-(4-methylpiperidino)-3-(2',4'-dichloro-4-biphenylyl)-butan-3-ol,
1-(4-methylpiperidino)-3-(2',4'-dibromo-4-biphenylyl)-butan-3-ol,
1-(4-methylpiperidino)-3-p-phenoxy-phenyl-butan-3-ol,
1-(4-methylpiperidino)-3-(4-o-fluorophenoxy-phenyl)-butan-3-ol,
1-(4-methylpiperidino)-3-(4-fluorophenoxy-phenyl)-butan-3-ol, 1-(4-methylpiperidino)-3-(4-o-chlorophenoxy-phenyl)-butan-3-ol,
1-(4-methylpiperidino)-3-(4-p-chlorophenoxy-phenyl)-butan-3-ol, m.p. 81° – 82°,
1-(4-methylpiperidino)-3-(4-o-bromophenoxy-phenyl)-butan-3-ol,
1-(4-methylpiperidino)-3-(4-p-bromophenoxy-phenyl)-butan-3-ol, m.p. 78° – 79.5°,
1-(4-methylpiperidino)-3-[4-(2,4-difluorophenoxy)-phenyl]-butan-3-ol,
1-(4-methylpiperidino)-3-[4-(2,4-dichlorophenoxy)-phenyl]-butan-3-ol,
1-(4-methylpiperidino)-3-[4-(2,4-dibromophenoxy)-phenyl]-butan-3-ol,
1-homopiperidino-3-p-biphenylyl-butan-3-ol, m.p. 66° – 67°,
1-homopiperidino-3-(2'-fluoro-4-biphenylyl)-butan-3-ol, hydrochloride, m.p. 160° – 161°,
1-homopiperidino-3-(4'-fluoro-4-biphenylyl)-butan-3-ol,
1-homopiperidino-3-(2'-chloro-4-biphenylyl)-butan-3-ol,
1-homopiperidino-3-(4'-chloro-4-biphenylyl)-butan-3-ol,
1-homopiperidino-3-(2'-bromo-4-biphenylyl)-butan-3-ol,
1-homopiperidino-3-(4'bromo-4-piphenylyl)-butan-3-ol,
1-homopiperidino-3-(2', 4'-difluoro-4-biphenylyl)-butan-3-ol,
1-homopiperidono-4-(2',4'-dichloro-4biphenylyl)-butan-3-ol,
1-homopiperidino-3-(2', 4'-dibromo-4-biphenylyl)-butan-3-ol,
1-homopiperidino-3-p-phenoxy-phenyl-butan-3-ol,
1-homopiperidino-3-(4-o-fluorophenoxy-phenyl)-butan-3-ol,
1-homopiperidino-3-(4-p-fluorophenoxy-phenyl)-butan-3-ol,
1-homopiperidino-3-(4-o-chlorophenoxy-phenyl)-butan-3-ol,
1-homopiperidino-4-(4-p-chlorophenoxy-phenyl)-butan-3-ol, hydrochloride, m.p. 180° – 181°,
1-homopiperidino-3-(4-o-bromophenoxy-phenyl)-butan-3-ol,
1-homopiperidino-3-(4-p-bromophenoxy-phenyl)-butan-3-ol,
1-homopiperidino-4-[4-(2,4-difluorophenoxy)-phenyl]-butan-3-ol,
1-homopiperidino-3-[4-(2,4-dichlorophenoxy)-phenyl]-butan-3-ol,
1-homopiperidino-3-[4-(2,4-dibromophenoxy)-phenyl]-butan-3-ol,
1-piperazino-3-p-biphenylyl-butan-3-ol,
1-piperazino-3-(2'-fluoro-4-biphenylyl)-butan-3-ol,
1-piperazino-3-(4'-fluoro-4-biphenylyl)-butan-3-ol, m.p. 168° – 169°,
1-piperazino-3-(2'-chloro-4-biphenylyl)-butan-3-ol,
1-piperazino-3-(4'-chloro-4-biphenylyl)-butan-3-ol,
1-piperazino-3-(2'-bromo-4-biphenylyl)-butan-3-ol,
1-piperazino-3-(4'-bromo-4-biphenylyl)-butan-3-ol,
1-piperazino-3-(2',4'-difluoro-4-biphenylyl)-butan-3-ol,
1-piperazino-3-(2',4'-dichloro-4-biphenylyl)-butan-3-ol,
1-piperazino-3-(2',4'-dibromo-4-biphenylyl)-butan-3-ol,
1-piperazino-3-p-phenoxy-phenyl-butan-3-ol,
1-piperazino-3-(4-o-fluorophenoxy-phenyl)-butan-3-ol,
1-piperazino-3-(4-p-fluorophenoxy-phenyl)-butan-3-ol,
1-piperazino-3-(4-o-chlorophenoxy-phenyl)-butan-3-ol,
1-piperazino-3-(4-p-chlorophenoxy-phenyl)-butan-3-ol,
1-piperazino-3-(4-o-bromophenoxy-phenyl)-butan-3-ol,
1-piperazino-3-(4-p-bromophenoxy-phenyl)-butan-3-ol,
1-piperazino-3-[4-(2,4-difluorophenoxy)-phenyl]-butan-3-ol,
1-piperazino-3-[4-(2,4-dichlorophenoxy)-phenyl]-butan-3-ol and
1-piperazino-3-[4-(2,4-dibromophenoxy)-phenyl]-butan-3-ol.

EXAMPLE 31

The following are obtained, analogously to Example 29, from the corresponding chlorine or bromine compounds, using di-n-propylamine, diisopropylamine, di-n-butylamine, diisobutylamine, di-n-pentylamine, di-n-hexylamine, 2-dimethylamino-ethylamine, 2-diethylamino-ethylamine, 3-dimethylamino-propylamine, 2-methylpiperidine, 3-methylpiperidine, 2,6-dimethylpiperidine, 1-methylpiperazine, 1-ethylpiperazine, 1-n-hexylpiperazine or 1-(2-hydroxyethyl)-piperazine:

1-Di-n-propylamino-3-p-biphenylyl-butan-3-ol,
1-di-n-propylamino-3-(4'-fluoro-4-biphenylyl)-butan-3-ol,
1-di-n-propylamino-3-(4'-chloro-4-biphenylyl)-butan-3-ol,
1-di-n-propylamino-3-(4-p-chlorophenoxy-phenyl)-butan-3ol,
1-diisopropylamino-3-p-biphenylyl-butan-3ol,
1-diisopropylamino-3-(4'-fluoro-4-biphenylyl)-butan-3-ol,
1-diisopropylamino-3-(4'-chloro-4-biphenylyl)-butan-3-ol,
1-diisopropylamino-3-(4-p-chlorophenoxy-phenyl)-butan-3-ol,
1-di-n-butylamino-3-p-biphenylyl-butan-3-ol,
1-di-n-butylamino-3-(4'-fluoro-4-biphenylyl)-butan-3-ol,
1-di-n-butylamino-3-(4'-chloro-4-biphenylyl)-butan-3-ol,
1-di-n-butylamino-3-(4-p-chlorophenoxy-phenyl)-butan-3-ol,
1-diisobutylamino-3-p-biphenylyl-butan-3-ol,
1-diisobutylamino-3-(4'-fluoro-4-biphenylyl)-butan-3-ol,
1-diisobutylamino-3-(4'-chloro-4-biphenylyl)-butan-3-ol,
1-diisobutylamino-3-(4-p-chlorophenoxy-phenyl)-butan-3-ol,
1-di-n-pentylamino-3-p-biphenylyl-butan-3-ol,
1-di-n-penthylamino-3-(4'-fluoro-4-biphenylyl)-butan-3-ol,
1-di-n-pentylamino-3-(4'-chloro-4-biphenylyl)-butan-3-ol,
1-di-n-pentylamino-3-(4-p-chlorophenoxy-phenyl)-butan-3-ol,
1-di-n-hexylamino-3-p-biphenylyl-butan-3-ol,
1-di-n-hexylamino-3-(4'-fluoro-4-biphenylyl)-butan-3-ol,
1-di-n-hexylamino-3-(4'-chloro-4-biphenylyl)-butan-3-ol,
1-di-n-hexylamino-3-(4-p-chlorophenoxy-phenyl)-butan-3-ol,
1-(2-dimethylamino-ethylamino)-3-p-biphenylyl-butan-3-ol,
1-(2-dimethylamino-ethylamino)-3-(4'-fluoro-4-biphenylyl)-butan-3-ol,
1-(2-dimethylamino-ethylamino)-3-(4'-chloro-4biphenylyl)-butan-3-ol,
1-(2-dimethylamino-ethylamino)-3-(4-p-chlorophenoxy-phenyl)-butan-3-ol, 1-(2-diethylamino-ethylamino)-3-p-biphenylyl-butan-3-ol,
1-(2-diethylamino-ethylamino)-3-(4'-fluoro-4-biphenylyl)-butan-3-ol, m.p. 74°; dihydrochloride, m.p. 198°,
1-(2-diethylamino-ethylamino)-3-(4'-chloro-4-biphenylyl)-butan-3-ol,
1-(2-diethylamino-ethylamino)-3-(4-p-chlorophenoxy-phenyl)-butan-3-ol,
1-(3-dimethylamino-propylamino)-3-p-biphenylyl-butan-3-ol,
1-(3-dimethylamino-propylamino)-3-(4'-fluoro-4-biphenylyl)-butan-3-ol,
1-(3-dimethylamino-propylamino)-3-(4'-chloro-4-biphenylyl)-butan-3-ol,
1-(3-dimethylamino-propylamino)-3-(4-p-chlorophenoxy-phenyl)-butan-3-ol,
1-(2-methylpiperidino)-3-p-biphenylyl-butan-3-ol,
1-(2-methylpiperidino)-3-(4'-fluoro-4-biphenylyl)-butan-3-ol,
1-(2-methylpiperidino)-3-(4'-chloro-4-biphenylyl)-butan-3ol,
1-(2-methylpiperidino)-3-(4-p-chlorophenoxy-phenyl)-butan-3-ol,
1-(3-methylpiperidino)-3-p-biphenylyl-butan-3-ol,
1-(3-methylpiperidino)-3-(4'-fluoro-4-biphenylyl)-butan-3-ol,
1-(3-methylpiperidino)-3-(4'-chloro-4-biphenylyl)-butan-3-ol,
1-(3-methylpiperidino)-3-(4-p-chlorophenoxy-phenyl)-butan-3-ol,
1-(2,6-dimethylpiperidino)-3-p-biphenylyl-butan-3-ol,
1-(2,6-dimethylpiperidino)-3-(4'-fluoro-4-biphenylyl)-butan-3-ol,
1-(2,6-dimethylpiperidino)-3-(4'-chloro-4-biphenylyl)-butan-3-ol,
1-(2,6-dimethylpiperidino)-3-(4-p-chlorophenoxy-phenyl)-butan-3-ol,
1-(4-methyl-piperazino)-3-p-biphenylyl-butan-3-ol,
1-(4-methyl-piperazino)-3-(4'-fluoro-4-biphenylyl)-butan-3-ol,
1-(4-methyl-piperazino)-3-(4'-chloro-4-biphenylyl)-butan-3-ol,
1-(4-methyl-piperazino)-3-(4-p-chlorophenoxy-phenyl)-butan-3-ol,
1-(4-ethyl-piperazino)-3-p-biphenylyl-butan-3-ol,
1-(4-ethyl-piperazino)-3-(4'-fluoro-4-biphenylyl)-butan-3-ol,
1-(4-ethyl-piperazino)-3-(4'-chloro-4-biphenylyl)-butan-3-ol,
1-(4-ethyl-piperazino)-3-(4-p-chlorophenoxy-phenyl)-butan-3-ol,
1-(4-n-hexyl-piperazino)-3-p-biphenylyl-butan-3-ol,
1-(4-n-hexylpiperazino)-3-(4'-fluoro-4-biphenylyl)-butan-3-ol,
1-(4-n-hexyl-piperazino)-3-(4'-chloro-4-biphenylyl)-butan-3-ol,
1-(4-n-hexyl-piperazino)-3-(4-p-chlorophenoxy-phenyl)-butan-3-ol,
1-[4-(2-hydroxyethyl)-piperazino]-3-p-biphenylyl-butan-3-ol,
1-[4-(2-hydroxyethyl)-piperazino]-3-(4'-fluoro-4-biphenylyl)-butan-3-ol, m.p. 76° – 78°; dihydrochloride, m.p. 246° – 247°,
1-[4-(2-hydroxyethyl)-piperazino]-3-(4'-chloro-4-biphenylyl)-butan-3-ol and
1-[4-(2-hydroxyethyl)-piperazino]-3-(4-p-chlorophenoxyphenyl)-butan-3-ol.

EXAMPLE 32

2.6 g of 1-chloro-3-p-biphenylyl-butan-3-ol are heated with 30 ml of diethylamine at 150° for 15 hours in an autoclave, and the mixture is cooled and worked up in the customary manner to give 1-diethylamino-3-p-biphenylyl-butan-3-ol.

The following are obtained analogously from the corresponding chlorine or bromine compounds:
1-Diethylamino-3-(2'-fluoro-4-biphenylyl)-butan-3ol,
1-diethylamino-3-(4'-fluoro-4-biphenylyl)-butan-3-ol,
1-diethylamino-3-(2'-chloro-4-biphenylyl)-butan-3-ol,
1-diethylamino-3-(4'-chloro-4-biphenylyl)-butan-3-ol, m.p. 61-63°,
1-diethylamino-3-(2'-bromo-4-biphenylyl)-butan-3-ol,
1-diethylamino-3-(4'-bromo-4-biphenylyl)-butan-3-ol,
1-diethylamino-3-(2',4'-difluoro-4-biphenylyl)-butan-3-ol,
1-diethylamino-3-(2',4'-dichloro-4-biphenylyl)-butan-3-ol,
1-diethylamino-3-(4',4'-dibromo-4-biphenylyl)-butan-3-ol,
1-diethylamino-3-p-phenoxy-phenyl-butan-3-ol,
1-diethylamino-3-(4-o-fluorophenoxy-phenyl)-butan-3-ol,
1-diethylamino-3-(4-p-fluorophenoxy-phenyl)-butan-3-ol,
1-diethylamino-3-(4-o-chlorophenoxy-phenyl)-butan-3-ol,
1-diethylamino-3-(4-p-chlorophenoxy-phenyl)-butan-3-ol,
1-diethylamino-3-(4-o-bromophenoxy-phenyl)-butan-3-ol,
1-diethylamino-3-(4-p-bromophenoxy-phenyl)-butan-3-ol,
1-diethylamino-3-[4-(2,4-difluorophenoxy)-phenyl]-butan-3-ol,
1-diethylamino-3-[4-(2,4-dichlorophenoxy)-phenyl]-butan-3-ol and
1-diethylamino-3-[4-(2,4-dibromophenoxy)-phenyl]-butan-3-ol.

EXAMPLE 33

A mixture of 2.6 g of 1-chloro-3-p-biphenylyl-butan-3-ol, 2.04 g of potassium phthalimide and 40 ml of DMF is heated at 110° for 1.5 hours. After cooling, the mixture is worked up in the customary manner to give 1-phthalimido-3-p-biphenylyl-butan-3-ol, m.p. 153° – 155°.

The following are obtained analogously from the corresponding chlorine or bromine compounds:
1-Phthalimido-3-(2'-fluoro-4-biphenylyl)-butan-3-ol, m.p. 125° –127°,
1-phthalimido-3-(4'-fluoro-4-biphenylyl)-butan-3-ol, m.p. 150° –152°,
1-phthalimido-3-(2'-chloro-4-biphenylyl)-butan-3-ol.
1phthalimido-3-(4'-chloro-4-biphenylyl)-butan-3-ol, m.p. 177°– 179 ,
1-phthalimido-3-(2'-bromo-4-biphenylyl)-butan-3-ol,
1-phthalimido-3-(4'-bromo-4-biphenylyl)-butan-3-ol,
1-phthalimido-3-(2',4'-difluoro-4-biphenylyl)-butan-3-ol, m.p. 128° – 130°,
1-phthalimido-3-(2',4'-dichloro-4-biphenylyl)-butan-3-ol,
1-phthalimido-3-(2',4'-dibromo-4-biphenylyl)-butan-3-ol,
1-phthalimido-3-p-phenoxy-phenyl-butan-3-ol, 1-phthalimido-3-(4-o-fluorophenoxy-phenyl)-butan-3-ol,
1-phthalimido-3-(4-p-fluorophenoxy-phenyl)-butan-3-ol,
1-phthalimido-3-(4-o-chlorophenoxy-phenyl)-butan-3-ol,
1-phthalimido-3-(4-p-chlorophenoxy-phenyl)-butan-3-ol, m.p. 135° − 137°,
1-phthalimido-3-(4-o-bromophenoxy-phenyl)-butan-3-ol,
1-phthalimido-3-(4-p-bromophenoxy-phenyl)-butan-3-ol,
1-phthalimido-3-[4-(2,4-difluorophenoxy)-phenyl]-butan-3-ol,
1-phthalimido-3-[4-(2,4-dichlorophenoxy)-phenyl]-butan-3-ol and
1-phthalimido-3-[4-(2,4-dibromophenoxy)-phenyl]-butan-3-ol.

EXAMPLE 34

A mixture of 2.6 g of 1-chloro-3-p-biphenylyl-butan-3-ol and 1.36 g of imidazole is heated at 140° for 3 hours. After cooling and working up in the customary manner, 1-(1-imidazolyl)-3-p-biphenylyl-butan-3-ol is obtained.

The following are obtained analogously from the corresponding chlorine or bromine compounds:
1-(1-imidazolyl)-3-(2'-fluoro-4-biphenylyl)-butan-3-ol,
1-(1-imidazolyl)-3-(4'-fluoro-4-biphenylyl)-butan-3-ol, m.p. 205° − 207°,
1-(1-imidazolyl)-3-(2'-chloro-4-biphenylyl)-butan-3-ol,
1-(1-imidazolyl)-3-(4'-chloro-4-biphenylyl)-butan-3-ol, m.p. 201° − 203°,
1-(1-imidazolyl)-3-(2'-bromo-4-biphenylyl)-butan-3-ol,
1-(1-imidazolyl)-3-(4'-bromo-4-biphenylyl)-butan-3-ol,
1-(1-imidazolyl)-3-(2',4'-difluoro-4-biphenylyl)-butan-3-ol,
1-(1-imidazolyl)-3-(2',4'-dichloro-4-biphenylyl)-butan-3-ol,
1-(1-imidazolyl)-3-(2',4'-dibromo-4-biphenylyl)-butan-3-ol,
1-(1-imidazolyl)-3-p-phenoxy-phenoxy-phenyl-butan-3-ol,
1-(1-imidazolyl)-3-(4-o-fluorophenoxy-phenyl)-butan-3-ol,
1-(1-imidazolyl)-3-(4-p-fluorophenoxy-phenyl)-butan-3-ol,
1-(1-imidazolyl)-3-(4-o-chlorophenoxy-phenyl)-butan-3-ol,
1-(1-imidazolyl)-3-(4-p-chlorophenoxy-phenyl)-butan-3-ol, m.p. 125° − 125°,
1-(1-imidazolyl)-3-(4-o-bromophenoxy-phenyl)-butan-3-ol,
1-(1-imidazolyl)-3-(4-p-bromophenoxy-phenyl)-butan-3-ol,
1-(1-imidazolyl)-3-[4-(2,4-difluorophenoxy)-phenyl]-butan-3-ol,
1-(1-imidazolyl)-3-[4-(2,4-dichlorophenoxy)-phenyl]-butan-3-ol, $n_D^{20}$ 1.5972, and
1-(1-imidazolyl)-3-[4-(2,4-dibromophenoxy)-phenyl]-butan-3-ol.

EXAMPLE 35

2.26 g of 3-p-biphenylybutan-1-ol are dissolved in 10 ml of isopropylamine and, after adding 0.5 g of Raney nickel, the solution is shaken for 15 hours at 160° in a tube. After cooling, filtering off the catalyst and evaporating, 1-isopropylamino-3-p-biphenylyl-butane is obtained.

EXAMPLE 36

3.48 g of 1-bis-(2-hydroxyethyl)-3-(4'-chloro-4-biphenylyl)-butane [obtainable from 1-chloro-3-(4'-chloro-4-biphenylyl)-butane and diethanolamine] are dissolved in 100 ml of xylene, 2 drops of $H_2SO_4$ are added and the mixture is boiled for an hour. After cooling and working up in the customary manner, 1-morpholino-3-(4'-chloro-4-biphenylyl)butane, m.p. 77° − 79°, is obtained.

EXAMPLE 37

0.1 g of p-toluenesulfonic acid is added to a solution of 3.48 g of 1-bis-(2-hydroxyethyl)-3-(4'-chloro-4-biphenylyl)-butane and 0.61 g of 2-aminoethanol in 100 ml of toluene and the mixture is boiled for 2.5 hours and cooled. After working up in the customary manner, 1-[4-(2-hydroxyethyl)-piperazino]-3-(4'-chloro-4-biphenylyl)-butane is obtained.

EXAMPLE 38

3 ml of concentrated hydrochloric acid are added at 0° to 3.26 g of 1-morpholino-3-(4'-amino-4-biphenylyl)-butan-3-ol [obtainable by nitrating 1-morpholino-3-(4-biphenylyl)-butan-3-ol and reducing the resulting 1-morpholino-3-(4'-nitro-4-biphenylyl)-butan-3-ol], and a solution of 1.4 g of $NaNO_2$ in 6 ml of water is then added at 0°, while stirring. After adding a solution of 0.7 g of boric acid in 1.5 g of 60% hydrofluoric acid, the mixture is stirred for 40 minutes and the product is filtered off, washed with water, methanol and ether and dried. The resulting diazonium salt is heated at about 150° until decomposition is complete. This gives 1-morpholino-3-(4'-fluoro-4-biphenylyl)-butan-3-ol.

EXAMPLE 39

3.26 g of 1-morpholino-3-(4'-amino-4-biphenylyl-butan-3-ol are dissolved in 30 ml of 10% hydrochloric acid, 0.7 g of $NaNO_2$ in 2 ml of water is added at 0° to 5°, the resulting diazonium salt solution is added dropwise, slowly, to a hot solution of $Cu_2Cl_2$ (obtained by reducing 2.1 g of copper sulfate with $SO_2$ in 13 ml of water, in the presence of 2.6 g of NaCl), and the mixture is heated to 90° to 95° for a further 30 minutes, cooled and worked up in the customary manner to give 1-morpholino-3-(4'-chloro-4-biphenylyl)-butan-3-ol, m.p. 106° − 108°.

EXAMPLE 40

1-morpholino-3-(4'-bromo-4-biphenylyl)-butan-3-ol, m.p. 97° − 99°, is obtained analogously to Example 39 using $Cu_2Br_2$ (instead of $Cu_2Cl_2$).

EXAMPLE 41

A mixture of 2.22 g of p-iodofluorobenzene and 2.71 g of the sodium salt of 1-piperidino-4-p-hydroxyphenyl-butan-3-ol (obtainable by reacting p-hydroxyacetophenone with bromoacetic acid ethyl ester and zinc, reducing the resulting 3-p-hydroxyphenyl-3-hydroxybutyric acid ethyl ester by means of $LiAlH_4$ to give 3-p-hydroxyphenyl-butane-1,3-diol reaction with $SOCl_2$ to give 1-chloro-3-p-hydroxyphenyl-butan-3-ol and reaction with iperidine) is warmed to 90° for 8 hours in the presence of 1 g of copper powder in 10 ml of HMPT and is then worked up in the customary manner. This gives 1-piperidino-4-(p-fluorophenoxyphenyl)-butan-3-ol.

EXAMPLE 42

A solution of 3.59 g of 1-piperidino-4-p-iodophenyl-butan-3-ol (obtainable by reacting 1-chloro-3-p-iodophenyl-butan-3-ol with piperidine) and 1.51 g of sodium p-chlorophenolate in 20 ml of DMF is heated at 130° for 8 hours. After working up in the customary manner, 1-piperidino-3-(4-p-chlorophenoxy-phenyl)-butan-3-ol, m.p. 73° – 75°, is obtained.

EXAMPLE 43

25.9 g of 3-(4'-fluoro-4-biphenylyl)-3-hydroxybutylamine p-toluenesulfonate are boiled with 1 g of p-toluenesulfonic acid in 500 ml of toluene for 2 hours under a water separator, and the mixture is cooled and worked up with sodium hydroxide solution to give 3-(4'-fluoro-4-biphenylyl)-2-buten-1-yl-amine.

The following are obtained analogously by dehydrating the corresponding hydroxyamines using p-toluenesulfonic acid:
1-Methylamino-3-p-biphenylyl-2-butene,
1-methylamino-3-(4'-fluoro-4-biphenylyl)-2-butene,
1-methylamino-3-(4'-chloro-4-biphenylyl)-2-butene,
1-methylamino-3-(4-p-chlorophenoxy-phenyl)-2-butene,
1-ethylamino-3-p-biphenylyl-2-butene,
1-ethylamino-3-(4'-fluoro-4-biphenylyl)-2-butene,
1-ethylamino-3-(4'-chloro-4-biphenylyl)-2-butene,
1-ethylamino-3-(4-p-chlorophenoxy-phenyl)-2-buene,
1-n-propylamino-3-p-biphenylyl-2-butene,
1-n-propylamino-3-(4'-fluoro-4-biphenylyl)-2-butene,
1-n-propylamino-3-(4'-chloro-4-biphenylyl)-2-butene,
1-n-propylamino-3-(4-p-chlorophenoxy-phenyl)-2-butene,
1-isopropylamino-3-p-biphenylyl-2-butene,
1-isopropylamino-3-(4'-fluoro-4-biphenylyl)-2-butene,
1-isopropylamino-3-(4'-chloro-4-biphenylyl)-2-butene,
1-isopropylamino-3-(4-p-chlorophenoxy-phenyl)-2-butene,
1-n-butylamino-3-p-biphenylyl-2-butene,
1-n-butylamino-3-(4'-fluoro-4-biphenylyl)-2-butene,
1-n-butylamino-3-(4'-chloro-4-biphenylyl)-2-butene,
1-n-butylamino-3-(4-p-chlorophenoxy-phenyl)-2-butene,
1-isobutylamino-3-p-biphenylyl-2-butene,
1-isobutylamino-3-(4'-fluoro-4-biphenylyl)-2-butene,
1-isobutylamino-3-(4'-chloro-4-biphenylyl)-2-butene,
1-isobutylamino-3-(4-p-chlorophenoxy-phenyl)-2-butene,
1-sec.-butylamino-3-p-biphenylyl-2-butene,
1-sec.-butylamino-3-(4'-fluoro-4-biphenylyl)-2-butene,
1-sec.-butylamino-3-(4'-chloro-4-biphenylyl)-2-butene,
1-sec.-butylamino-3-(4-p-chlorophenoxy-phenyl)-2-butene,
1-tert.-butylamino-3-p-biphenylyl-2-butene,
1-tert.-butylamino-3-(4'-fluoro-4-biphenylyl)-2-butene,
1-tert.-butylamino-3-(4'-chloro-4-biphenylyl)-2-butene and
1-tert.-butylamino-3-(4-p-chlorophenoxy-phenyl)-2-butene.

EXAMPLE 44

A mixture of 3.1 g of 1-morpholino-3-biphenylyl-butan-3-ol, 0.1 g of benzenesulfonic acid and 80 ml of benzene is boiled for 24 hours under a water separator. After working up in the customary manner, 1-morpholino-3-p-biphenylyl-2-butene is obtained.

The following are obtained analogously by dehydrating the corresponding hydroxyamines:
1-Morpholino-3-(2'-fluoro-4-biphenylyl)-2-butene,
1-morpholino-3-(4'-fluoro-4-biphenylyl)-2-butene,
1-morpholino-3-(2'-chloro-4-biphenylyl)-2-butene,
1-morpholino-3-(4'-chloro-4-biphenylyl)-2-butene, m.p. 109°–111°,
1-morpholino-3-(2'-bromo-4-biphenylyl)-2-butene,
1-morpholino-3-(4'-bromo-4-biphenylyl)-2-butene,
1-morpholino-3-(2',4'-difluoro-4-biphenylyl)-2-butene,
1-morpholino-3-(2',4'-dichloro-4-biphenylyl)-2-butene,
1-morpholino-3-(2',4'-dibromo-4-biphenylyl)-2-butene,
1-morpholino-3-p-phenoxy-phenyl-2-butene,
1-morpholino-3-(4-o-fluorophenoxy-phenyl)-2-butene,
1-morpholino-3-(4-p-fluorophenoxy-phenyl)-2-butene,
1-morpholino-3-(4-o-chlorophenoxy-phenyl)-2-butene,
1-morpholino-3-(4-p-chlorophenoxy-phenyl)-2-butene, m.p. 95°–97°,
1-morpholino-3-(4-o-bromophenoxy-phenyl)-2-butene,
1-morpholino-3-(4-p-bromophenoxy-phenyl)-2-butene,
1-morpholino-3-[4-(2,4-difluorophenoxy)-phenyl]-2-butene,
1-morpholino-3-[4-(2,4-dichlorophenoxy)-phenyl]-2-butene,
1-morpholino-3-[4-(2,4-dibromophenoxy)-phenyl]-2-butene,
1-morpholino-4-p-biphenylyl-3-pentene,
1-morpholino-(4'-fluoro-4-biphenylyl)-3-pentene,
1-morpholino-(4'-chloro-4-biphenylyl)-3-pentene,
1-morpholino-(4'-bromo-4-biphenylyl)-3-pentene,
1-morpholino-(4-p-chlorophenoxy-phenyl)-3-pentene,
1-pyrrolidino-3-p-biphenylyl-2-butene,
1-pyrrolidino-3-(2'-fluoro-4-biphenylyl)-2-butene,
1-pyrrolidino-3-(4'-fluoro-4-biphenylyl)-2-butene,
1-pyrrolidino-3-(2'-chloro-4-biphenylyl)-2-butene,
1-pyrrolidino-3-(4'-chloro-4-biphenylyl)-2-butene,
1-pyrrolidino-3-(2'-bromo-4-biphenylyl)-2-butene,
1-pyrrolidino-3-(4'-bromo-4-biphenylyl)-2-butene,
1-pyrrolidino-3-(2',4'-difluoro-4biphenylyl)-2-butene,
1-pyrrolidino-3-(2',4'-dichloro-4-biphenylyl)-2-butene,
1-pyrrolidino-3-(2',4'-dibromo-4-biphenylyl)-2-butene,
1-pyrrolidino-3-p-phenoxy-phenyl-2-butene,
1-pyrrolidino-3-(4-o-fluorophenoxy-phenyl)-2-butene,
1-pyrrolidino-3-(4-p-fluorophenoxy-phenyl)-2-butene,
1-pyrrolidino-3-(4-o-chlorophenoxy-phenyl)-2-butene,
1-pyrrolidino-3-(4-p-chlorophenoxy-phenyl)-2-butene,
1-pyrrolidino-3-(4-o-bromophenoxy-phenyl)-2-butene,
1-pyrrolidino-3-(4-p-bromophenoxy-phenyl)-2-butene,
1-pyrrolidino-3-[4-(2,4-difluorophenoxy)-phenyl]-2-butene,
1-pyrrolidino-3-[4-(2,4-dichlorophenoxy)-phenyl]-2-butene,
1-pyrrolidino-3-[4-(2,4-dibromophenoxy)-phenyl]-2-butene,
1-piperidino-3-p-biphenylyl-2-butene,
1-piperidino-3-(2'-fluoro-4-biphenylyl)-2-butene,
1-piperidino-3-(4'-fluoro-4-biphenylyl)-2-butene,
1-piperidino-3-(2'-chloro-4-biphenylyl)-2-butene,
1-piperidino-3-(4'-chloro-4-biphenylyl)-2-butene,
1-piperidino-3-(2'-bromo-4-biphenylyl)-2-butene,
1-piperidino-3-(4'-bromo-4-biphenylyl)-2-butene, m.p. 130°–132°,
1-piperidino-3-(2',4'-difluoro-4-biphenylyl)-2-butene,
1-piperidino-3-(2',4'-dichloro-4-biphenylyl)-2-butene,
1-piperidino-3-(2',4'-dibromo-4-biphenylyl)-2-butene,
1-piperidino-3-p-phenoxy-phenyl-2-butene,
1-piperidino-3-(4-o-fluorophenoxy-phenyl)-2-butene,
1-piperidino-3-(4-p-fluorophenoxy-phenyl)-2-butene, 1-piperidino-3-(4-o-chlorophenoxy-phenyl)-2-butene,
1-piperidino-3-(4-p-chlorophenoxy-phenyl)-2-butene,
1-piperidino-3-(4-o-bromophenoxy-phenyl)-2-butene,
1-piperidino-3-(4-p-bromophenoxy-phenyl)-2-butene,
1-piperidino-3-[4-(2,4-difluorophenoxy)-phenyl]-2-butene,
1-piperidino-3-[4-(2,4-dichlorophenoxy)-phenyl]-2-butene,
1-piperidino-3-[4-(2,4-dibromophenoxy)-phenyl]-2-butene,
1-piperidino-4-p-biphenylyl-3-pentene,
1-piperidino-4-(4'-fluoro-4-biphenylyl)-3-pentene,
1-piperidino-4-(4'-chloro-4-biphenylyl)-3-pentene,
1-piperidino-4-(4'-bromo-4-biphenylyl)-3-pentene,
1-piperidino-4-(4-p-chlorophenoxy-phenyl)-3-pentene,
1-(4-methylpiperidino)-3-p-biphenylyl-2-butene,
1-(4-methylpiperidino)-3-(2'-fluoro-4-biphenylyl)-2-butene,
1-(4-methylpiperidino)-3-(4'-fluoro-4-biphenylyl)-2-butene,
1-(4-methylpiperidino)-3-(2'-chloro-4-biphenylyl)-2-butene,
1-(4-methylpiperidino)-3-(4'-chloro-4-biphenylyl)-2-butene,
1-(4-methylpiperidino)-3-(2'-bromo-4-biphenylyl)-2-butene,
1-(4-methylpiperidino)-3-(4'-bromo-4-biphenylyl)-2-butene,
1-(4-methylpiperidino)-3-(2',4'-difluoro-4-biphenylyl)-2-butene,
1-(4-methylpiperidino)-3-(2',4'-dichloro-4-biphenylyl)-2-butene,
1-(4-methylpiperidino)-3-(2',4'-dibromo-4-biphenylyl)-2-butene,
1-(4-methylpiperidino)-3-p-phenoxy-phenyl-2-butene,
1-(4methylpiperidino)-3-(4-o-fluorophenoxy-phenyl)-2-butene,
1-(4-methylpiperidino)-3-(4-p-fluorophenoxy-phenyl)-2-butene,
1-(4-methylpiperidino)-3-(4-o-chlorophenoxy-phenyl)-2-butene,
1-(4-methylpiperidino)-3-(4-p-chlorophenoxy-phenyl)-2-butene,
1-(4-methylpiperidino)-3-(4-o-bromophenoxy-phenyl)-2-butene,
1-(4-methylpiperidino)-3-(4-p-bromophenoxy-phenyl)-2-butene,
1-(4-methylpiperidino)-3-[4-(2,4-difluorophenoxy)-phenyl]-2-butene,
1-(4-methylpiperidino)-3-[4-(2,4-dichlorophenoxy)-phenyl]-2-butene,
1-(4-methylpiperidino)-3-[4-(2,4-dibromophenoxy)-phenyl]-2-butene,
1-homopiperidino-3-p-biphenylyl-2-butene,
1-homopiperidino-3-(2'-fluoro-4-biphenylyl)-2-butene,
1-homopiperidino-3-(4'-fluoro-4-biphenylyl)-2-butene,
1-homopiperidino-3-(2'-chloro-4-biphenylyl)-2-butene,
1-homopiperidino-3-(4'-chloro-4-biphenylyl)-2-butene,
1-homopiperidino-3-(2'-bromo-4-biphenylyl)-2-butene,
1-homopiperidino-3-(4'-bromo-4-biphenylyl)-2-butene,
1-homopiperidino-3-(2',4'-difluoro-4-biphenylyl)-2-butene,
1-homopiperidino-3-(2',4'-dichloro-4-biphenylyl)-2-butene,
1-homopiperidino-3-(2',4'-dibromo-4-biphenylyl)-2-butene,
1-homopiperidino-3-p-phenoxy-phenyl-2-butene,
1-homopiperidino-3-(4-o-fluorophenoxy-phenyl)-2-butene,
1-homopiperidino-3-(4-p-fluorophenoxy-phenyl)-2-butene,
1-homopiperidino-3-(4-o-chlorophenoxy-phenyl)-2-butene,
1-homopiperidino-3-(4-p-chlorophenoxy-phenyl)-2-butene,
1-homopiperidino-3-(4-o-bromophenoxy-phenyl)-2-butene,
1-homopiperidino-3-(4-p-bromophenoxy-phenyl)-2-butene,
1-homopiperidino-3-[4-(2,4-difluorophenoxy)-phenyl]-2-butene,
1-homopiperidino-3-[4-(2,4-dichlorophenoxy)-phenyl]-2-butene,
1-homopiperidino-3-[4-(2,4-dibromophenoxy)-phenyl]-2-butene,
1-piperazino-3-p-biphenylyl-2-butene,
1-piperidino-3-(2'-fluoro-4-biphenylyl)-2-butene,
1-piperazino-3-(4'-fluoro-4-biphenylyl)-2-butene,
1-piperazino-3-(2'-chloro-4-biphenylyl)-2-butene,
1-piperazino-3-(4'-chloro-4-biphenylyl)-2-butene,
1-piperazino-3-(2'-bromo-4-biphenylyl)-2-butene,
1-piperazino-3-(4'-bromo-4-biphenylyl)-2-butene,
1-piperazino-3-(2',4'-difluoro-4-biphenylyl)-2-butene,
1-piperazino-3-(2',4'-dichloro-4-biphenylyl)-2-butene,
1-piperazino-3-(2',4'-dibromo-4-biphenylyl)-2-butene,
1-piperazino-3-p-phenoxy-phenyl-2-butene,
1-piperazino-3-(4-o-fluorophenoxy-phenyl)-2-butene,
1-piperazino-3-(4-p-fluorophenoxy-phenyl)-2-butene,
1-piperazino-3-(4-o-chlorophenoxy-phenyl)-2-butene,
1-piperazino-3-(4-p-chlorophenoxy-phenyl)-2-butene,
1-piperazino-3-(4-o-bromophenoxy-phenyl)-2-butene,
1-piperazino-3-(4-p-bromophenoxy-phenyl)-2-butene,
1-piperazino-3-[4-(2,4-difluorophenoxy)-phenyl]-2-butene,
1-piperazino-3-[4-(2,4-dichlorophenoxy)-phenyl]-2-butene,
1-piperazino-3-[4-(2,4-dibromophenoxy)-phenyl]-2-butene,
1-diethylamino-3-p-biphenylyl-2-butene,
1-diethylamino-3-(2'-fluoro-4-biphenylyl)-2-butene,
1-diethylamino-3-(4'-fluoro-4-biphenylyl)-2-butene,
1-diethylamino-3-(2'-chloro-4-biphenylyl)-2-butene,
1-diethylamino-3-(4'-chloro-4-biphenylyl)-2-butene,
1-diethylamino-3-(2'-bromo-4-biphenylyl)-2-butene,
1-diethylamino-3-(4'-bromo-4-biphenylyl)-2-butene,
1-diethylamino-3-(2',4'-difluoro-4-biphenylyl)-2-butene,
1-diethylamino-3-(2',4'-dichloro-4-biphenylyl)-2-butene,
1-diethylamino-3-(2',4'-dibromo-4-biphenylyl)-2-butene,
1-diethylamino-3-p-phenoxy-phenyl-2-butene,
1-diethylamino-3-(4-o-fluorophenoxy-phenyl)-2-butene,
1-diethylamino-3-(4-p-fluorophenoxy-phenyl)-2-butene,
1-diethylamino-3-(4-o-chlorophenoxy-phenyl)-2-butene,
1-diethylamino-3-(4-p-chlorophenoxy-phenyl)-2-butene,
1-diethylamino-3-(4o-bromophenoxy-phenyl)-2-butene,
1-diethylamino-3-(4-p-bromophenoxy-phenyl)-2-butene,
1-diethylamino-3-[4-(2,4-difluorophenoxy)-phenyl]-2-butene,
1-diethylamino-3-[4-(2,4-dichlorophenoxy)-phenyl]-2-butene, 1-diethylamino-3-[4-(2,4-dibromophenoxy)-phenyl]-2-butene,
1-phthalimido-3-p-biphenylyl-2-butene,
1-phthalimido-3-(2'-fluoro-4-biphenylyl)-2-butene,
1-phthalimido-3-(4'-fluoro-4-biphenylyl)-2-butene,
1-phthalimido-3-(2'-chloro-4-biphenylyl)-2-butene,
1-phthalimido-3-(4'-chloro-4-biphenylyl)-2-butene, m.p. 188°–191°,
1-phthalimido-3-(2'-bromo-4-biphenylyl)-2-butene,
1-phthalimido-3-(4'-bromo-4-biphenylyl)-2-butene,
1-phthalimido-3-(2',4'-difluoro-4-biphenylyl)-2-butene,
1-phthalimido-3-(2',4'-dichloro-4-biphenylyl)-2-butene,
1-phthalimido-3-(2',4'-dibromo-4-biphenylyl)-2-butene,
1-phthalimido-3-p-phenoxy-phenyl-2-butene,
1-phthalimido-3-(4-o-fluorophenoxy-phenyl)-2-butene,
1-phthalimido-3-(4-p-fluorophenoxy-phenyl)-2-butene,
1-phthalimido-3-(4-o-chlorophenoxy-phenyl)-2-butene,
1-phthalimido-3-(4-p-chlorophenoxy-phenyl)-2-butene,
1-phthalimido-3-(4-o-bromophenoxy-phenyl)-2-butene,
1-phthalimido-3-(4-p-bromophenoxy-phenyl)-2-butene,
1-phthalimido-3-[4-(2,4-difluorophenoxy)-phenyl]-2-butene,
1-phthalimido-3-[4-(2,4-dichlorophenoxy)-phenyl]-2-butene,
1-phthalimido-3-[4-(2,4-dibromophenoxy)-phenyl]-2-butene,
1-(1-imidazolyl)-3-p-biphenylyl-2-butene,
1-(1-imidazolyl)-3-(2'-fluoro-4-biphenylyl)-2-butene,
1-(1-imidazolyl)-3-(4'-fluoro-4-biphenylyl)-2-butene,
1-(1-imidazolyl)-3-(2'-chloro-4-biphenylyl)-2-butene,
1-(1-imidazolyl)-3-(4'-chloro-4-biphenylyl)-2-butene,
1-(1-imidazolyl)-3-(2'-bromo-4-biphenylyl)-2-butene,
1-(1-imidazolyl)-3-(4'-bromo-4-biphenylyl)-2-butene,
1-(1-imidazolyl)-3-(2',4'-difluoro-4-biphenylyl)-2-butene,
1-(1-imidazolyl)-3-(2',4'-dichloro-4-biphenylyl)-2-butene,
1-(1-imidazolyl)-3-(2',4'-dibromo-4-biphenylyl)-2-butene,
1-(1-imidazolyl)-3-p-phenoxy-phenyl-2-butene,
1-(1-imidazolyl)-3-(4-o-fluorophenoxy-phenyl)-2-butene,
1-(1-imidazolyl)-3-(4-p-fluorophenoxy-phenyl)-2-butene,
1-(1-imidazolyl)-3-(4-o-chlorophenoxy-phenyl)-2-butene,
1-(1-imidazolyl)-3-(4-p-chlorophenoxy-phenyl)-2-butene, m.p. 79°–81°,
1-(1-imidazolyl)-3-(4-o-bromophenoxy-phenyl)-2-butene,
1-(1-imidazolyl)-3-(4-p-bromophenoxy-phenyl)-2-butene,
1-(1-imidazolyl)-3-[4-(2,4-difluorophenoxy)-phenyl]-2-butene,
1-(1-imidazolyl)-3-[4-(2,4-dichlorophenoxy)-phenyl]-2-butene $n_D^{20}$ 1.5671, and
1-(1-imidazolyl)-3-[4-(2,4-dibromophenoxy)-phenyl]-2-butene.

EXAMPLE 45

The following are obtained analogously to Example 44 by dehydrating the corresponding hydroxyamines:
1-Di-n-propylamino-3-p-biphenylyl-2-butene,
1-di-n-propylamino-3-(4'-fluoro-4-biphenylyl)-2-butene,
1-di-n-propylamino-3-(4'-chloro-4-biphenylyl)-2-butene,
1-di-n-propylamino-3-(4-p-chlorophenoxy-phenyl)-2-butene,
1-diisopropylamino-3-p-biphenylyl-2-butene,
1-diisopropylamino-3-(4'-fluoro-4-biphenylyl)-2-butene,
1-diisopropylamino-3-(4'-chloro-4-biphenylyl)-2-butene,
1-diisopropylamino-3-(4-p-chlorophenoxy-phenyl)-2-butene,
1-di-n-butylamino-3-p-biphenylyl-2-butene,
1-di-n-butylamino-3-(4'-fluoro-4-biphenylyl)-2-butene,
1-di-n-butylamino-3-(4'-chloro-4-biphenylyl)-2-butene,
1-di-n-butylamino-3-(4-p-chlorophenoxy-phenyl)-2-butene,
1-diisobutylamino-3-p-biphenylyl-2-butene,
1-diisobutylamino-3-(4'-fluoro-4-biphenylyl)-2-butene,
1-diisobutylamino-3-(4'-chloro-4-biphenylyl)-2-butene,
1-diisobutylamino-3-(4-p-chlorophenoxy-phenyl)-2-butene,
1-di-n-pentylamino-3-p-biphenylyl-2-butene,
1-di-n-pentylamino-3-(4'-fluoro-4-biphenylyl)-2-butene,
1-di-n-pentylamino-3-(4'-chloro-4-biphenylyl)-2-butene,
1-di-n-pentylamino-3-(4-p-chlorophenoxy-phenyl)-2-butene,
1-di-n-hexylamino-3-p-biphenylyl-2-butene,
1-di-n-hexylamino-3-(4'-fluoro-4-biphenylyl)-2-butene,
1-di-n-hexylamino-3-(4'-chloro-4-biphenylyl)-2-butene,
1-di-n-hexylamino-3-(4-p-chlorophenoxy-phenyl)-2-butene,
1-(2-dimethylamino-ethylamino)-3-p-biphenylyl-2-butene,
1-(2-dimethylamino-ethylamino)-3-(4'-fluoro-4-biphenylyl)-2-butene,
1-(2-dimethylamino-ethylamino)-3-(4'-chloro-4-biphenylyl)-2-butene,
1-(2-dimethylamino-ethylamino)-3-(4-p-chlorophenoxy-phenyl)-2-butene,
1-(2-diethylamino-ethylamino)-3-p-biphenylyl-2-butene,
1-(2-diethylamino-ethylamino)-3-(4'-fluoro-4-biphenylyl)-2-butene,
1-(2-diethylamino-ethylamino)-3-(4'-chloro-4-biphenylyl)-2-butene,
1-(2-diethylamino-ethylamino)-3-(4-p-chlorophenoxy-phenyl)-2-butene,
1-(3-dimethylamino-propylamino)-3-p-biphenylyl-2-butene,
1-(3-dimethylamino-propylamino)-3-(4'-fluoro-4-biphenylyl)-2-butene,
1-(3-dimethylamino-propylamino)-3-(4'-chloro-4-biphenylyl)-2-butene,
1-(3-dimethylamino-propylamino)-3-(4-p-chlorophenoxy-phenyl)-2-butene,
1-(2-methylpiperidino)-3-p-biphenylyl-2-butene,
1-(2-methylpiperidino)-3-(4'-fluoro-4-biphenylyl)-2-butene,
1-(2-methylpiperidino)-3-(4'-chloro-4-biphenylyl)-2-butene,
1-(2-methylpiperidino)-3-(4-p-chlorphenoxy-phenyl)-2-butene,
1-(3-methylpiperidino)-3-p-biphenylyl-2-butene,
1-(3-methylpiperidino)-3-(4'-fluoro-4-biphenylyl)-2-butene,
1-(3-methylpiperidino)-3-(4'-chloro-4-biphenylyl)-2-butene,
1-(3-methylpiperidino)-3-(4-p-chlorophenoxy-phenyl)-2-butene,
1-(2,6-dimethylpiperidino)-3-p-biphenylyl-2-butene,
1-(2,6-dimethylpiperidino)-3-(4'-fluoro-4-biphenylyl)-2-butene, 1-(2,6-dimethylpiperidino)-3-(4'-chloro-4-biphenylyl)-2-butene,
1-(2,6-dimethylpiperidino)-3-(4-p-chlorophenoxyphenyl)-2-butene,
1-(4-methyl-piperazino)-3-p-biphenylyl-2-butene,
1-(4-methyl-piperazino)-3-(4'-fluoro-4-biphenylyl)-2-butene,
1-(4-methyl-piperazino)-3-(4'-chloro-4-biphenylyl)-2-butene,
1-(4-methyl-piperazino)-3-(4-p-chlorophenoxy-phenyl)-2-butene,
1-(4-ethyl-piperazino)-3-p-biphenylyl-2-butene,
1-(4-ethyl-piperazino)-3-(4'-fluoro-4-biphenylyl)-2-butene,
1-(4-ethyl-piperazino)-3-(4'-chloro-4-biphenylyl)-2-butene,
1-(4-ethyl-piperazino)-3-(4-p-chlorophenoxy-phenyl)-2-butene,
1-(4-n-hexyl-piperazino)-3-p-biphenylyl-2-butene,
1-(4-n-hexyl-piperazino)-3-(4'-fluoro-4-biphenylyl)-2-butene,
1-(4-n-hexyl-piperazino)-3-(4'-chloro-4-biphenylyl)-2-butene,
1-(4-n-hexyl-piperazino)-3-(4-p-chlorophenoxyphenyl)-2-butene,
1-[4-(2-hydroxyethyl)-piperazino]-3-p-biphenylyl-2-butene,
1-[4-(2-hydroxyethyl)-piperazino]-3-(4'-fluoro-4-biphenylyl)-2-butene,
1-[4-(2-hydroxyethyl)-piperazino]-3-(4'-chloro-4-biphenylyl)-2-butene and
1[4-(2-hydroxyethyl)-piperazino]-3-(4-p-chlorophenoxy-phenyl)-2-butene.

EXAMPLE 46

A mixture of 1 g of 3-(4'-chloro-4-biphenylyl)-3-hydroxy-butylamine, 2.5 ml of a 67% solution of HI in acetic acid and 5 ml of acetic acid is boiled for 90 minutes, evaporated and worked up using water and chloroform. This gives 3-(4'-chloro-4-biphenylyl)-butylamine hydriodide, which is converted into the free base employing a sodium hydroxide solution. Tartrate, m.p. 200° – 202°.

The following are obtained analogously from the corresponding hydroxyamines, using HI/acetic acid:
1-Methylamino-3-p-biphenylyl-butane,
1-methylamino-3-(4'-fluoro-4-biphenylyl)-butane,
1-methylamino-3-(4'-chloro-4-biphenylyl)-butane,
1-methylamino-3-(4-p-chlorophenoxy-phenyl)-butane,
1-ethylamino-3-p-biphenylyl-butane,
1-ethylamino-3-(4'-fluoro-4-biphenylyl)-butane,
1- ethylamino-3-(4'-chloro-4-biphenylyl)-butane,
1-ethylamino-3-(4-p-chlorophenoxy-phenyl)-butane,
1-n-propylamino-3-p-biphenylyl-butane,
1-n-propylamino-3-(4'-fluoro-4-biphenylyl)-butane,
1-n-propylamino-3-(4'-chloro-4-biphenylyl)-butane,
1-n-propylamino-3-(4-p-chlorophenoxy-phenyl)-butane,
1-isopropylamino-3-p-biphenylyl-butane,
1-isopropylamino-3-(4'-fluoro-4-biphenylyl)-butane,
1-isopropylamino-3-(4'-chloro-4-biphenyl)-butane,
1-isopropylamino-3-(4-p-chlorophenoxy-phenyl)-butane,
1-n-butylamino-3-p-biphenylyl-butane,
1-n-butylamino-3-(4'-fluoro-4-biphenylyl)-butane,
1-n-butylamino-3-(4'-chloro-4biphenylyl)-butane,
1-n-butylamino-3-(4-p-chlorophenoxy-phenyl)-butane,
1-isobutylamino-3-p-biphenylyl-butane,
1-isobutylamino-3-(4'-fluoro-4-biphenylyl)-butane,
1-isobutylamino-3-(4'-chloro-4-biphenylyl)-butane,
1-isobutylamino-3-(4-p-chlorophenoxy-phenyl)-butane,
1-sec.-butylamino-3-p-biphenylyl-butane,
1-sec.-butylamino-3-(4'-fluoro-4-biphenylyl)-butane,
1-sec.-butylamino-3-(4'-chloro-4-biphenylyl)-butane,
1-sec.-butylamino-3-(4-p-chlorophenoxy-phenyl)-butane,
1-tert.-butylamino-3-p-biphenylyl-butane,
1-tert.-butylamino-3-(4'-fluoro-4-biphenylyl)-butane,
1-tert.-butylamino-3-(4'-chloro-4-biphenylyl)-butane and
1-tert.-butylamino-3-(4-p-chlorophenoxy-phenyl)-butane.

EXAMPLE 47

A mixture of 3.1 g of 1-morpholino-3-p-biphenylyl-butan-3-ol, 10 ml of 67% hydriodic acid and 18 ml of acetic acid is heated at 150° for 1.5 hours. 1-Morpholino-3-p-biphenylyl-butane is obtained after cooling and working up in the customary manner.

The following are obtained analogously by reducing the corresponding hydroxyamines:
1-Morpholino-2-p-biphenylyl-propane,
1-morpholino-2-(4'-fluoro-4-biphenylyl)-propane,
1-morpholino-2-(4'-chloro-4-biphenylyl)-propane,
1-morpholino-2-(4'-bromo-4-biphenylyl)-propane,
1-morpholino-2-(4-p-chlorophenoxy-phenyl)-propane,
1-morpholino-3-(2'-fluoro-4-biphenylyl)-butane,
1-morpholino-3-(4'-fluoro-4-biphenylyl)-butane, m.p. 54° – 56°,
1-morpholino-3-(2'-chloro-4-biphenylyl)-butane,
1-morpholino-3-(4'-chloro-4-biphenylyl)-butane, m.p. 77° – 79°,
1-morpholino-3-(2'-bromo-4-biphenylyl)-butane,
1-morpholino-3-(4'-bromo-4-biphenyl)-butane,
1-morpholino-3-(2',4'-difluoro-4-biphenylyl)-butane, hydrochloride, m.p. 198° –200°,
1-morpholino-3-(2',4'-dichloro-4-biphenylyl)-butane,
1-morpholino-3-(2',4'-dibromo-4-biphenylyl)-butane,
1-morpholino-3-p-phenoxy-phenyl-butane,
1-morpholino-3-(4-o-fluorophenoxy-phenyl)-butane,
1-morpholino-3-(4-p-fluorophenoxy-phenyl)-butane,
1-morpholino-3-(4-o-chlorophenoxy-phenyl)-butane,
1-morpholino-3-(4-p-chlorophenoxy-phenyl)-butane, hydrochloride, m.p. 172° – 174°,
1-morpholino-3-(4-o-bromophenoxy-phenyl)-butane,
1-morpholino-3-(4-p-bromophenoxy-phenyl)-butane,
1-morpholino-3-[4-(2,4-difluorophenoxy)-phenyl]-butane,
1-morpholino-3-[4-(2,4-dichlorophenoxy)-phenyl]-butane,
1-morpholino-3-[4-(2,4-dibromophenoxy)-phenyl]-butane,
1-morpholino-4-p-biphenylyl-pentane,
1-morpholino-4-(4'-fluoro-4-biphenylyl)-pentane,
1-morpholino-4-(4'-chloro-4-biphenylyl)-pentane,
1-morpholino-4-(4'-bromo-4-biphenylyl)-pentane,
1-morpholino-4-(4-p-chlorophenoxy-phenyl)-pentane,
1-pyrrolidino-3-p-biphenylyl-butane,
1-pyrrolidino-3-(2'-fluoro-4-biphenylyl)-butane,
1-pyrrolidino-3-(4'-fluoro-4-biphenylyl)-butane,
1-pyrrolidino-3-(2'-chloro-4-biphenylyl)-butane,
1-pyrrolidino-3-(4'-chloro-4-biphenylyl)-butane,
1-pyrrolidino-3-(2'-bromo-4-biphenylyl)-butane,
1-pyrrolidino-3-(4'-bromo-4-biphenylyl)-butane,
1-pyrrolidino-3-(2',4'-difluoro-4-biphenylyl)-butane,
1-pyrrolidino-3-(2',4'-dichloro-4-biphenylyl)-butane, 1-pyrrolidino-3-(2',4'-dibromo-4-biphenylyl)-butane,
1-pyrrolidino-3-p-phenoxy-phenyl-butane,
1-pyrrolidino-3-(4-o-fluorophenoxy-phenyl)-butane,
1-pyrrolidino-3-(4-p-fluorophenoxy-phenyl)-butane,
1-pyrrolidino-3-(4-o-chlorophenoxy-phenyl)-butane,
1-pyrrolidino-3-(4-p-chlorophenoxy-phenyl)-butane,
1-pyrrolidino-3-(4-o-bromophenoxy-phenyl)-butane,
1-pyrrolidino-3-(4-p-bromophenoxy-phenyl)-butane,
1-pyrrolidino-3-[4-(2,4-difluorophenoxy)-phenyl]-butane,
1-pyrrolidino-3-[4-(2,4-dichlorophenoxy)-phenyl]-butane,
1-pyrrolidino-3-[4-(2,4-dibroophenoxy)-phenyl]-butane,
1-piperidino-2-p-biphenylyl-propane,
1-piperidino-2-(4'-fluoro-4-biphenylyl)-propane,
1-piperidino-2-(4'-chloro-4-biphenylyl)-propane,
1-piperidino-2-(4'-bromo-4-biphenylyl)-propane, hydrochloride, m.p. 260° – 261°,
1-piperidino-2-(4-p-chlorophenoxy-phenyl)-propane,
1-piperidino-3-p-biphenylyl-butane,
1-piperidino-3-(4'-fluoro-4-biphenylyl)-butane, hydrochloride, m.p. 207° – 209°,
1-piperidino-3-(2'-chloro-4-biphenylyl)-butane,
1-piperidino-3-(4'-chloro-4-biphenylyl)-butane, hydrochloride, m.p. 215°,
1-piperidino-3-(2'-bromo-4-biphenylyl)-butane,
1-piperidino-3-(4'-bromo-4-biphenylyl)-butane,
1-piperidino-3-(2',4'-difluoro-4-biphenylyl)-butane,
1-piperidino-3-(2',4'-dichloro-4-biphenylyl)-butane,
1-piperidino-3(2',4'-dibromo-4-biphenylyl)-butane,
1-piperidino-3-p-phenoxy-phenyl-butane,
1-piperidino-3-(4-o-fluorophenoxy-phenyl)-butane,
1-piperidino-3-(4-p-fluorophenoxy-phenyl)-butane,
1-piperidino-3-(4-o-chlorophenoxy-phenyl)-butane,
1-piperidino-3-(4-p-chlorophenoxy-phenyl)-butane,
1-piperidino-3-(4-o-bromophenoxy-phenyl)-butane,
1-piperidino-3-(4-p-bromophenoxy-phenyl)-butane,
1-piperidino-3-[4-(2,4-difluorophenoxy)-phenyl]-butane,
1-piperidino-3-[4-(2,4-dichlorophenoxy)-phenyl]-butane,
1-piperidino-3-[4-(2,4-dibromophenoxy)-phenyl]-butane,
1-piperidino-4-p-biphenylyl-pentane,
1-piperidino-4-(4'-fluoro-4-biphenylyl)-pentane,
1-piperidino-4-(4'-chloro-4-biphenylyl)-pentane,
1-piperidino-4-(4'-bromo-4-biphenylyl)-pentane, hydrochloride, m.p. 235°; hydriodide, m.p. 212° – 214°,
1-piperidino-4-(4-p-chlorophenoxy-phenyl)-pentane,
1-(4-methylpiperidino)-3-p-biphenylyl-butane,
1-(4-methylpiperidino)-3-(2'-fluoro-4-biphenylyl)-butane,
1-(4-methylpiperidino)-3-(4'-fluoro-4-biphenylyl)-butane,
1-(4-methylpiperidino)-3-(2'-chloro-4-biphenylyl)-butane,
1-(4-methylpiperidino)-3-(4'-chloro-4-biphenylyl)-butane,
1-(4-methylpiperidino)-3-(2'-bromo-4-biphenylyl)-butane,
1-(4-methylpiperidino)-3-(4'-bromo-4-biphenylyl)-butane,
1-(4-methylpiperidino)-3-(2',4'-difluoro-4-biphenylyl)-butane,
1-(4-methylpiperidino)-3-(2',4'-dichloro-4-biphenylyl)-butane,
1-(4-methylpiperidino)-3-(2',4'-dibromo-4-biphenylyl)-butane,
1-(4-methylpiperidino)-3-p-phenoxy-phenyl-butane,
1-(4-methylpiperidino)-3-(4-o-fluorophenoxy-phenyl)-butane,
1-(4-methylpiperidino)-3-(4-p-fluorophenoxy-phenyl)-butane,
1-(4-methylpiperidino)-3-(4-o-chlorophenoxy-phenyl)-butane,
1-(4-methylpiperidino)-3-(4-p-chlorophenoxy-phenyl)-butane,
1-(4-methylpiperidino)-3-(4-o-bromophenoxy-phenyl)-butane
1-(4-methylpiperidino)-3-(4-p-bromophenoxy-phenyl)-butane,
1-(4-methylpiperidino)-3-[4-(2,4-difluorophenoxy)-phenyl]-butane,
1-(4-methylpiperidino)-3-[4-(2,4-dichlorophenoxy)-phenyl]-butane,
1-(4-methylpiperidino)-3-[4-(2,4-dibromophenoxy)-phenyl]-butane,
1-homopiperidino-3-p-biphenylyl-butane,
1-homopiperidino-3-(2'-fluoro-4-biphenylyl)-butane,
1-homopiperidino-3-(4'-fluoro-4-biphenylyl)-butane,
1-homopiperidino-3-(2'-chloro-4-biphenylyl)-butane,
1-homopiperidino-3-(4'-chloro-4-biphenylyl)-butane,
1-homopiperidino-3-(2'-bromo-4-biphenylyl)-butane,
1-homopiperidino-3-(4'-bromo-4-biphenylyl)-butane,
1-homopiperidino-3-(2',4'-difluoro-4-biphenylyl)-butane,
1-homopiperidino-3-(2',4'-dichloro-4-biphenylyl)-butane,
1-homopiperidino-3-(2',4'-dibromo-4-biphenylyl)-butane,
1-homopiperidino-3-p-phenoxy-phenyl-butane,
1-homopiperidino-3-(4-o-fluorophenoxy-phenyl)-butane,
1-homopiperidino-3-(4-p-fluorophenoxy-phenyl)-butane,
1-homopiperidino-3-(4-o-chlorophenoxy-phenyl)-butane,
1-homopiperidino-3-(4-p-chlorophenoxy-phenyl)-butane,
1-homopiperidino-3-(4-o-bromophenoxy-phenyl)-butane,
1-homopiperidino-3-(4-p-bromophenoxy-phenyl)-butane,
1-homopiperidino-3-[4-(2,4-difluorophenoxy)-phenyl]-butane,
1-homopiperidino-3-[4-(2,4-dichlorophenoxy)-phenyl]-butane,
1-homopiperidino-3-[4-(2,4-dibromophenoxy)-phenyl]-butane,
1-piperazino-3-p-biphenylyl-butane,
1-piperazino-3-(2'-fluoro-4-biphenylyl)-butane,
1-piperazino-3-(4'-fluoro-4-biphenylyl)-butane, m.p. 67°–69°,
1-piperazino-3-(2'-chloro-4-biphenylyl)-butane,
1-piperazino-3-(4'-chloro-4-biphenylyl)-butane,
1-piperazino-3-(2'-bromo-4-biphenylyl)-butane,
1-piperazino-3-(4'-bromo-4-biphenylyl)-butane,
1-piperazino-3-(2',4'-difluoro-4-biphenylyl)-butane,
1-piperazino-3-(2',4'-dichloro-4-biphenylyl)-butane,
1-piperazino-3-(2',4'-dibromo-4-biphenylyl)-butane,
1-piperazino-3-p-phenoxy-phenyl-butane,
1-piperazino-3-(4-o-fluorophenoxy-phenyl)-butane,
1-piperazino-3-(4-p-fluorophenoxy-phenyl)-butane,
1-piperazino-3-(4-o-chlorophenoxy-phenyl)-butane,
1-piperazino-3-(4-p-chlorophenoxy-phenyl)-butane,
1-piperazino-3-(4-o-bromophenoxy-phenyl)-butane, 1-piperazino-3-(4-p-bromophenoxy-phenyl)-butane,
1-piperazino-3-[4-(2,4-difluorophenoxy)-phenyl]-butane,
1-piperazino-3-[4-(2,4-dichlorophenoxy)-phenyl]-butane,
1-piperazino-3-[4-(2,4-dibromophenoxy)-phenyl]-butane,
1-diethylamino-3-p-biphenylyl-butane,
1-diethylamino-3-(2'-fluoro-4-biphenylyl)-butane,
1-diethylamino-3-(4'-fluoro-4-biphenylyl)-butane,
1-diethylamino-3-(2'-chloro-4-biphenylyl)-butane,
1-diethylamino-3-(4'-chloro-4-biphenylyl)-butane, m.p. 42°–44°, b.p. 175°–180°/0.1 mm,
1-diethylamino-3-(2'-bromo-4-biphenylyl)-butane,
1-diethylamino-3-(4'-bromo-4-biphenylyl)-butane,
1-diethylamino-3-(2',4'-difluoro-4-biphenylyl)-butane,
1-diethylamino-3-(2',4'-dichloro-4-biphenylyl)-butane,
1-diethylamino-3-(2',4'-dibromo-4-biphenylyl)-butane,
1-diethylamino-3-p-phenoxy-phenyl-butane,
1-diethylamino-3-(4-o-fluorophenoxy-phenyl)-butane,
1-diethylamino-3-(4-p-fluorophenoxy-phenyl)-butane,
1-diethylamino-3-(4-o-chlorophenoxy-phenyl)-butane,
1-diethylamino-3-(4-p-chlorophenoxy-phenyl)-butane,
1-diethylamino-3-(4-o-bromophenoxy-phenyl)-butane,
1-diethylamino-3-(4-p-bromophenoxy-phenyl)-butane,
1-diethylamino-3-[4-(2,4-difluorophenoxy)-phenyl]-butane,
1-diethylamino-3-[4-(2,4-dichlorophenoxy)-phenyl]-butane,
1-diethylamino-3-[4-(2,4-dibromophenoxy)-phenyl]-butane,
1-phthalimido-3-p-biphenylyl-butane, m.p. 120°–123°,
1-phthalimido-3-(2'-fluoro-4-biphenylyl)-butane, m.p. 75°–79°,
1-phthalimido-3-(4'-fluoro-4-biphenylyl)-butane, m.p. 142°–144°,
1-phthalimido-3-(2'-chloro-4-biphenylyl)-butane,
1-phthalimido-3-(4'-chloro-4-biphenylyl)-butane, m.p. 174°–176°,
1-phthalimido-3-(2'-bromo-4-biphenylyl)-butane,
1-phthalimido-3-(4'-bromo-4-biphenylyl)-butane, m.p. 180°–182°,
1-phthalimido-3-(2',4'-difluoro-4-biphenylyl)-butane, m.p. 95°–96°,
1-phthalimido-3-(2',4'-dichloro-4-biphenylyl)-butane,
1-phthalimido-3-(2',4'-dibromo-4-biphenylyl)-butane,
1-phthalimido-3-p-phenoxyphenyl-butane,
1-phthalimido-3-(4-o-fluorophenoxy-phenyl)-butane,
1-phthalimido-3-(4-p-fluorophenoxy-phenyl)-butane,
1-phthalimido-3-(4-o-chlorophenoxy-phenyl)-butane,
1-phthalimido-3-(4-p-chlorophenoxy-phenyl)-butane, m.p. 60°–62°,
1-phthalimido-3-(4-o-bromophenoxy-phenyl)-butane,
1-phthalimido-3-(4-p-bromophenoxy-phenyl)-butane,
1-phthalimido-3-[4-(2,4-difluorophenoxy)-phenyl]-butane,
1-phthalimido-3-[4-(2,4-dichlorophenoxy)-phenyl]-butane,
1-phthalimido-3-[4-(2,4-dibromophenoxy)-phenyl]-butane,
1-(1-imidazolyl)-3-p-biphenylyl-butane,
1-(1-imidazolyl)-3-(2'-fluoro-4-biphenylyl)-butane,
1-(1-imidazolyl)-3-(4'-fluoro-4-biphenylyl)-butane, m.p. 101°–103°,
1-(1-imidazolyl)-3-(2'-chloro-4-biphenylyl)-butane,
1-(1-imidazolyl)-3-(4'-chloro-4-biphenylyl)-butane, m.p. 129°–131°,
1-(1-imidazolyl)-3-(2'-bromo-4-biphenylyl)-butane,
1-(1-imidazolyl)-3-(4'-bromo-4-biphenylyl)-butane, hydrochloride, m.p. 230°–232°,
1-(1-imidazolyl)-3-(2',4'-difluoro-4-biphenylyl)-butane, hydrochloride, m.p. 81°–83°,
1-(1-imidazolyl)-3-(2',4'-dichloro-4-biphenylyl)-butane,
1-(1-imidazolyl)-3-(2',4'-dibromo-4-biphenylyl)-butane,
1-(1-imidazolyl)-3-p-phenoxy-phenyl-butane,
1-(1-imidazolyl)-3-(4-o-fluorophenoxy-phenyl)-butane,
1-(1-imidazolyl)-3-(4-p-fluorophenoxy-phenyl)-butane,
1-(1-imidazolyl)-3-(4-o-chlorophenoxy-phenyl)-butane,
1-(1-imidazolyl)-3-(4-p-chlorophenoxy-phenyl)-butane, m.p. 66°–70°,
1-(1-imidazolyl)-3-(4-o-bromophenoxy-phenyl)-butane,
1-(1-imidazolyl)-3-(4-p-bromophenoxy-phenyl)-butane,
1-(1-imidazolyl)-3-[4-(2,4-difluorophenoxy)-phenyl]-butane,
1-(1-imidazolyl)-3-[4-(2,4-dichlorophenoxy)-phenyl]-butane and
1-(1-imidazolyl)-3-[4-(2,4-dibromophenoxy)-phenyl]-butane.

EXAMPLE 48

The following are obtained, analogously to Example 47, by reducing the corresponding hydroxyamines, using HI:
1-di-n-propylamino-3-p-biphenylyl-butane,
1-di-n-propylamino-3-(4'-fluoro-4-biphenylyl)-butane,
1-di-n-propylamino-3-(4'-chloro-4-biphenylyl)-butane,
1-di-n-propylamino-3-(4-p-chlorophenoxy-phenyl)-butane,
1-diisopropylamino-3-p-biphenylyl-butane,
1-diisopropylamino-3-(4'-fluoro-4-biphenylyl)-butane,
1-diisopropylamino-3-(4'-chloro-4-biphenylyl)-butane,
1-diisopropylamino-3-(4-p-chlorophenoxy-phenyl)-butane,
1-di-n-butylamino-3-p-biphenylyl-butane,
1-di-n-butylamino-3-(4'-fluoro-4-biphenylyl)-butane,
1-di-n-butylamino-3-(4'-chloro-4-biphenylyl)-butane,
1-di-n-butylamino-3-(4-p-chlorophenoxy-phenyl)-butane,
1-diisobutylamino-3-p-biphenylyl-butane,
1-diisobutylamino-3-(4'-fluoro-4-biphenylyl)-butane,
1-diisobutylamino-3-(4'-chloro-4-biphenylyl)-butane,
1-diisobutylamino-3-(4-p-chlorophenoxy-phenyl)-butane,
1-di-n-pentylamino-3p-biphenylyl-butane,
1-di-n-pentylamino-3-(4'-fluoro-4-biphenylyl)-butane,
1-di-n-pentylamino-3-(4'-chloro-4-biphenylyl)-butane,
1-di-n-pentylamino-3-(4-p-chlorophenoxy-phenyl)-butane,
1-di-n-hexylamino-3-p-biphenylyl-butane,
1-di-n-hexylamino-3-(4'-fluoro-4-biphenylyl)-butane,
1-di-n-hexylamino-3-(4'-chloro-4-biphenylyl)-butane,
1-di-n-hexylamino-3-(4-p-chlorophenoxy-phenyl)-butane,
1-(2-dimethylamino-ethylamino)-3-p-biphenylyl-butane,
1-(2-dimethylamino-ethylamino)-3-(4'-fluoro-4-biphenylyl)-butane,
1-(2-dimethylamino-ethylamino)-3-(4'-chloro-4-biphenylyl)-butane,
1-(2-dimethylamino-ethylamino)-3-(4-p-chlorophenoxy-phenyl)-butane,
1-(2-diethylamino-ethylamino)-3-p-biphenylyl-butane,
1-(2-diethylamino-ethylamino)-3-(4'-fluoro-4-biphenylyl)-butane,
1-(2-diethylamino-ethylamino)-3-(4'-chloro-4-biphenylyl)-butane, 1-(2-diethylamino-ethylamino)-3-(4-p-chlorophenoxy-phenyl)-butane,
1-(3-dimethylamino-propylamino)-3-p-biphenylyl-butane,
1-(3-dimethylamino-propylamino)-3-(4'-fluoro-4-biphenylyl)-butane,
1-(3-dimethylamino-propylamino)-3-(4'-chloro-4-biphenylyl)-butane,
1-(3-dimethylamino-propylamino)-3-(4-p-chloro-phenoxy-phenyl)-butane,
1-(2-methylpiperidino)-3-p-biphenylyl-butane,
1-(2-methylpiperidino)-3-(4'-fluoro-4-biphenylyl)-butane,
1-(2-methylpiperidino)-3-(4'-chloro-4-biphenylyl)-butane,
1-(2-methylpiperidino)-3-(4-p-chlorophenoxy-phenyl)-butane,
1-(3-methylpiperidino)-3-p-biphenylyl-butane,
1-(3-methylpiperidino)-3-(4'-fluoro-4-biphenylyl)-butane,
1-(3-methylpiperidino)-3-(4'-chloro-4-biphenylyl)-butane,
1-(3-methylpiperidino)-3-(4-p-chlorophenoxy-phenyl)-butane,
1-(2,6-dimethylpiperidino)-3-p-biphenylyl-butane,
1-(2,6-dimethylpiperidino)-3-(4'-fluoro-4-biphenylyl)-butane,
1-(2,6-dimethylpiperidino)-3-(4'-chloro-4-biphenylyl)-butane,
1-(2,6-dimethylpiperidino)-3-(4-p-chlorophenoxy-phenyl)-butane,
1-(4-methyl-piperazino)-3-p-biphenylyl-butane,
1-(4-methyl-piperazino)-3-(4'-fluoro-4-biphenylyl)-butane,
1-(4-methyl-piperazino)-3-(4'-chloro-4-biphenylyl)-butane,
1-(4-methyl-piperazino)-3-(4-p-chlorophenoxy-phenyl)-butane,
1-(4-ethyl-piperazino)-3-p-biphenylyl-butane,
1-(4-ethyl-piperazino)-3-(4'-fluoro-4-biphenylyl)-butane,
1-(4-ethyl-piperazino)-3-(4'-chloro-4-biphenylyl)-butane,
1-(4-ethyl-piperazino)-3-(4-p-chlorophenoxy-phenyl)-butane,
1-(4-n-hexyl-piperazino)-3-p-biphenylyl-butane,
1-(4-n-hexyl-piperazino)-3-(4'-fluoro-4-biphenylyl)-butane,
1-(4-n-hexyl-piperazino)-3-(4'-chloro-4-biphenylyl)-butane,
1-(4-n-hexyl-piperazino)-3-(4-p-chlorophenoxy-phenyl)-butane,
1-[4-(2-hydroxyethyl)-piperazino]-3-p-biphenylyl-butane,
1-[4-(2-hydroxyethyl)-piperazino]-3-(4'-fluoro-4-biphenylyl)-butane,
1-[4-(2-hydroxyethyl)-piperazino]-3-(4'-chloro-4-biphenylyl)-butane and
1-[4-(2-hydroxyethyl)-piperazino]-3-(4-p-chloro-phenoxy-phenyl)-butane.

EXAMPLE 49

A solution of 24.1 g of 3-(4'-fluoro-4-biphenylyl)-2-buten-1-yl-amine in 500 ml of ethylacetate is hydrogenated, over 10 g of 5% Pd-on-charcoal at 20° and normal pressure until the absorption of hydrogen has ceased. The mixture is filtered and evaporated to give 3-(4'-fluoro-4-biphenylyl)-butylamine, hydrochloride, m.p. 222°–224°.

EXAMPLE 50

3.71 g of 1-phthalimido-3-p-biphenylyl-butan-3-ol are dissolved in 20 ml of acetic acid, a solution of 0.8 g of chlorine in 20 ml of acetic acid is added dropwise, while stirring, at 20°, and the mixture is stirred for a further hour and evaporated. 1-Phthalimido-3-(4'-chloro-4-biphenylyl)-butan-3-ol, m.p. 177°–179°, is obtained after working up in the customary manner.

EXAMPLE 51

1-Piperidino-3-(4'-bromo-4-biphenylyl)-butan-3-ol, m.p. 89°–91°, is obtained, analogously to Example 50, from 1-piperidino-3-p-biphenylyl-butan-3-ol, using an equivalent quantity of bromine in acetic acid.

EXAMPLE 52

A solution of 2.25 g of 3-p-biphenylyl-butylamine and 1.5 g of benzaldehyde in 25 ml of benzene is boiled for 2 hours under a water separator. The solution of the resulting 1-benzylidene-amino-3-p-biphenylyl-butane is heated with 5 g of methyliodide for 12 hours at 150° in a tube and is then evaporated. The resulting quaternary salt is boiled for 10 minutes in 90% ethanol. The mixture is evaporated again and taken up in dilute hydrochloric acid and the benzaldehyde which has been split off is extracted with ether. The acid aqueous solution is rendered alkaline by means of sodium hydroxide solution and worked up in the customary manner. This gives 1-methylamino-3-p-biphenylyl-butane.

EXAMPLE 53

A mixture of 2.62 g of 3-p-biphenylyl-butylamine hydrochloride, 5 ml of formic acid, 0.7 g of sodium formate and 4 ml of 40% formaldehyde solution is heated to 60° for 3 hours and then to 100° for 12 hours. 1-Dimethylamino-3-biphenylyl-butane is obtained after working up in the customary manner.

The following are obtained analogously from the corresponding primary amines:
1-Dimethylamino-3-(2'-fluoro-4-biphenylyl)-butane,
1-dimethylamino-3-(4'-fluoro-4-biphenylyl)-butane,
1-dimethylamino-3-(2'-chloro-4-biphenylyl)-butane,
1-dimethylamino-3-(4'-chloro-4-biphenylyl)-butane,
1-dimethylamino-3-(2'-bromo-4-biphenylyl)-butane,
1-dimethylamino-3-(4'-bromo-4-biphenylyl)-butane,
1-dimethylamino-3-(2',4'-difluoro-4-biphenylyl)-butane,
1-dimethylamino-3-(2',4'-dichloro-4-biphenylyl)-butane,
1-dimethylamino-3-(2',4'-dibromo-4-biphenylyl)-butane,
1-dimethylamino-3-p-phenoxy-phenyl-butane,
1-dimethylamino-3-(4-o-fluorophenoxy-phenyl)-butane,
1-dimethylamino-3-(4-p-fluorophenoxy-phenyl)-butane,
1-dimethylamino-3-(4-o-chlorophenoxy-phenyl)-butane,
1-dimethylamino-3-(4-p-chlorophenoxy-phenyl)-butane,
1-dimethylamino-3-(4-o-bromophenoxy-phenyl)-butane,
1-dimethylamino-3-(4-p-bromophenoxy-phenyl)-butane,
1-dimethylamino-3-[4-(2,4-difluorophenoxy)-phenyl]-butane,
1-dimethylamino-3-[4-(2,4-dichlorophenoxy)-phenyl]-butane and 1-dimethylamino-3-[4-(2,4-dibromophenoxy)-phenyl]-butane.

EXAMPLE 54

A mixture of 2.67 g of 1-isopropylamino-3-p-biphenylylbutane, 12 ml of formic acid and 2 g of 40% formaldehyde solution is heated at 60° for 3 hours and then at 100° for 12 hours and is then evaporated. 1-(N-Methyl-N-isopropylamino)-3-p-biphenylyl-butane is obtained after working up in the customary manner.

EXAMPLE 55

A mixture of 2.25 g of 3-p-biphenylyl-butylamine, 1.38 g of potassium carbonate, 2.53 g of 1,5-dibromopentane and 15 ml of n-butanol is boiled for 24 hours, while stirring. The mixture is filtered and the filtrate is evaporated and worked up in the customary manner to give 1-piperidino-3-p-biphenylyl-butane.

EXAMPLE 56

A mixture of 2.25 g of 3-p-biphenylyl-butylamine, 20 ml of benzene, 1 ml of pyridine and 1 ml of acetic anhydride is stirred for 3 hours at 25°. 1-Acetamido-3-p-biphenylylbutane is obtained after working up in the customary manner.

The following are obtained analogously by acetylating the corresponding primary or secondary amines:
1-Acetamido-3-(2′-fluoro-4-biphenylyl)-butane,
1-acetamido-3-(4′-fluoro-4-biphenylyl)-butane,
1-acetamido-3-(2′-chloro-4-biphenylyl)-butane,
1-acetamido-3-(4′-chloro-4-biphenylyl)-butane, m.p. 118° – 120°,
1-acetamido-3-(2′-bromo-4-biphenylyl)-butane,
1-acetamido-3-(4′-bromo-4-biphenylyl)-butane,
1-acetamido-3-(2′,4′-difluoro-4-biphenylyl)-butane,
1-acetamido-3-(2′,4′-dichloro-4-biphenylyl)-butane,
1-acetamido-3-(2′,4′-dibromo-4-biphenylyl)-butane,
1-acetamido-3-p-phenoxy-phenyl-butane,
1-acetamido-3-(4-o-fluorophenoxy-phenyl)-butane,
1-acetamido-3-(4-p-fluorophenoxy-phenyl)-butane,
1-acetamido-3-(4-o-chlorophenoxy-phenyl)-butane,
1-acetamido-3-(4-p-chlorophenoxy-phenyl)-butane,
1-acetamido-3-(4-o-bromophenoxy-phenyl)-butane,
1-acetamido-3-(4-p-bromophenoxy-phenyl)-butane,
1-acetamido-3-[4-(2,4-difluorophenoxy)-phenyl]-butane,
1-acetamido-3-[4-(2,4-dichlorophenoxy)-phenyl]-butane,
1-acetamido-3-[4-(2,4-dibromophenoxy)-phenyl]-butane,
1-acetamido-3-p-biphenylyl-3-butanol,
1-acetamido-3-(2′-fluoro-4-biphenylyl)-3-butanol,
1-acetamido-3-(4′-fluoro-4-biphenylyl)-3-butanol,
1-acetamido-3-(2′-chloro-4-biphenylyl)-3-butanol,
1-acetamido-3-(4′-chloro-4-biphenylyl)-3-butanol,
1-acetamido-3-(2′-bromo-4-biphenylyl)-3-butanol,
1-acetamido-3-(4′-bromo-4-biphenylyl)-3-butanol,
1-acetamido-3-(2′,4′-difluoro-4-biphenylyl)-3-butanol,
1-acetamido-3-(2′,4′-dichloro-4-biphenylyl)-3-butanol,
1-acetamido-3-(2′,4′-dibromo-4-biphenylyl)-3-butanol,
1-acetamido-3-p-phenoxy-phenyl-3-butanol,
1-acetamido-3-(4-o-fluorophenoxy-phenyl)-3-butanol,
1-acetamido-3-(4-p-fluorophenoxy-phenyl)-3-butanol,
1-acetamido-3-(4-o-chlorophenoxy-phenyl)-3-butanol,
1-acetamido-3-(4-p-chlorophenoxy-phenyl)-3-butanol,
1-acetamido-3-(4-o-bromophenoxy-phenyl)-3-butanol,
1-acetamido-3-(4-p-bromophenoxy-phenyl)-3-butanol,
1-acetamido-3-[4-(2,4-difluorophenoxy)-phenyl]-3-butanol,
1-acetamido-3-[4-(2,4-dichlorophenoxy)-phenyl]-3-butanol,
1-acetamido-3-[4-(2,4-dibromophenoxy)-phenyl]-3-butanol and
1-(N-methyl-acetamido)-3-p-biphenylyl-butan-3-ol.

EXAMPLE 57

A mixture of 2.6 g of 3-(4′-chloro-4-biphenylyl)-butylamine, 12 ml of pyridine and 1 ml of acetyl chloride is allowed to stand for 2 hours, decomposed with water and worked up in the customary manner to give 1-acetamido-3-(4′-chloro-4-biphenylyl)-butane, m.p. 118°– 120°.

The following are obtained analogously by acylating the corresponding primary or secondary amines:
1-Propionamido-3-p-biphenylyl-butane,
1-propionamido-3-(4′-fluoro-4-biphenylyl)-butane,
1-propionamido-3-(4′-chloro-4-biphenylyl)-butane,
1-propionamido-3-(4-p-chlorophenoxy-phenyl)-butane,
1-butyramido-3-p-biphenylyl-butane,
1-butyramido-3-(4′-fluoro-4-biphenylyl)-butane,
1-butyramido-3-(4′-chloro-4-biphenylyl)-butane,
1-butyramido-3-(4-p-chlorophenoxy-phenyl)-butane,
1-isobutyramido-3-p-biphenylyl-butane,
1-isobutyramido-3-(4′-fluoro-4-biphenylyl)-butane,
1-isobutyramido-3-(4′-chloro-4-biphenylyl)-butane, 1-isobutyramido-3-(4-p-chlorophenoxy-phenyl)-butane,
1-propionamido-3-p-biphenylyl-butan-3-ol,
1-propionamido-3-(4′-fluoro-4-biphenylyl)-butan-3-ol,
1-propionamido-3-(4′-chloro-4-biphenylyl)-butan-3-ol,
1-propionamido-3-(4-p-chlorophenoxy-phenyl)-butan-3-ol,
1-butyramido-3-p-biphenylyl-butan-3-ol,
1-butyramido-3-(4′-fluoro-4-biphenylyl)-butan-3-ol,
1-butyramido-3-(4′-chloro-4-biphenylyl)-butan-3-ol,
1-butyramido-3-(4-p-chlorophenoxy-phenyl)-butan-3-ol,
1-isobutyramido-3-p-biphenylyl-butan-3-ol,
1-isobutyramido-3-(4′-fluoro-4-biphenylyl)-butan-3-ol,
1-isobutyramido-3-(4′-chloro-4-biphenylyl)-butan-3-ol,
1-isobutyramido-3-(4-p-chlorophenoxy-phenyl)-butan-3-ol,
1-(N-methyl-propionamido)-3-p-biphenylyl-butan-3-ol,
1-valeramido-3-p-biphenylyl-butan-3-ol and
1-caproamido-3-p-biphenylyl-butan-3-ol.

EXAMPLE 58

2.25 g of 3-p-biphenylyl-butylamine and 5 g of phthalic anhydride are heated at 120° for 90 minutes, cooled and worked up in the customary manner to give 1-phthalimido-3-p-biphenylyl-butane, m.p. 120°– 123°.

EXAMPLE 59

A solution of 28.5 g of 1-acetamido-3-(4′-fluoro-4-biphenylyl)-butane in 800 ml of 10% methanolic KOH solution is boiled for 48 hours. The solution is concentrated and worked up using water and ether to give 3-(4′-fluoro-4-biphenylyl)-butylamine; hydrochloride, m.p. 222° – 224°.

EXAMPLE 60

37.3 g of 1-phthalimido-3-(4′-fluoro-4-biphenylyl)-butane are boiled for 6 hours with 400 ml of 20% aqueous hydrochloric acid, evaporated and worked up using sodium hydroxide solution and ether to give 3-(4′- fluoro-4-biphenylyl)-butylamine, hydrochloride, m.p. 222°–224°.

EXAMPLE 61

A solution of 3.55 g of 1-phthalimido-3-p-biphenylyl-butane and 1.25 ml of 80% hydrazine hydrate in 40 ml of methanol is boiled for 4 hours. 1-(3,4-Dihydro-4-oxo-1-phthalazinyl-amino)-3-p-biphenylyl-butane is precipitated by adding water.

The following are obtained analogously by hydrazinolysis of the corresponding phthalimides:
1-(3,4-Dihydro-4-oxo-1-phthalazinyl-amino)-3-(2'-fluoro-4-biphenylyl)-butane,
1-(3,4-dihydro-4-oxo-1-phthalazinyl-amino)-3-(4'-fluoro-4-biphenylyl)-butane, m.p. 150 – 168°,
1-(3,4-dihydro-4-oxo-1-phthalazinyl-amino)-3-(2'-chloro-4-biphenylyl)-butane,
1-(3,4-dihydro-4-oxo-1-phthalazinyl-amino)-3-(4'-chloro-4-biphenylyl)-butane, m.p. 195°,
1-(3,4-dihydro-4-oxo-1-phthalazinyl-amino)-3-(2'-bromo-4-biphenylyl)-butane,
1-(3,4-dihydro-4-oxo-1-phthalazinyl-amino)-3-(4'-bromo-4-biphenylyl)-butane,
1-(3,4-dihydro-4-oxo-1-phthalazinyl-amino)-3-(2',4'-difluoro-4-biphenylyl)-butane,
1-(3,4-dihydro-4-oxo-1-phthalazinyl-amino)-3(2',4'-dichloro-4-biphenylyl)-butane,
1-(3,4-dihydro-4-oxo-1-phthalazinyl-amino)-3-(2',4'-dibromo-4-biphenylyl)-butane,
1-(3,4-dihydro-4-oxo-1-phthalazinyl-amino)-3-p-phenoxy-phenyl-butane,
1-(3,4-dihydro-4-oxo-1-phthalazinyl-amino)-3-(4-o-fluorophenoxy-phenyl)-butane,
1-(3,4-dihydro-4-oxo-1-phthalazinyl-amino)-3-(4-p-fluorophenoxy-phenyl)-butane,
1-(3,4-dihydro-4-oxo-1-phthalazinyl-amino)-3-(4-o-chlorophenoxy-phenyl)-butane,
1-(3,4-dihydro-4-oxo-1-phthalazinyl-amino)-3-(4-p-chlorophenoxy-phenyl)-butane,
1-(3,4-dihydro-4-oxo-1-phthalazinyl-amino)-3-(4-o-bromophenoxy-phenyl)-butane,
1-(3,4-dihydro-4-oxo- 1-phthalazinyl-amino)-3-(4-p-bromophenoxy-phenyl)-butane,
1-(3,4-dihydro-4-oxo-1-phthalazinyl-amino)-3-[4-(2,4-difluorophenoxy)-phenyl]-butane,
1-(3,4-dihydrp-4-oxo-1-phthalazinyl-amino)3-[4-(2,4-dichlorophenoxy)-phenyl]-butane and
1-(3,4-dihydro-4-oxo-1-phthalazinyl-amino)-3-[4-(2,4-dibromophenoxy)-phenyl]-butane.

EXAMPLE 62

38.95 g of 1-phthalimido-3-(4'-chloro-4-biphenylyl)-butane are boiled with 12.2 ml of 80% hydrazine hydrate in 400 ml of ethanol for 2 hours, while stirring, water is added, the mixture is cooled and the resulting 1-(3,4-dihydro-4-oxo-1-phthalazinyl-amino)-3-(4'-chloro-4-biphenylyl)-butane (m.p. 195°) is filtered off, dissolved in 450 ml of ethanol and 450 ml of 37% hydrochloric acid and boiled for 30 minutes, while stirring. The solution is concentrated and worked up using sodium hydroxide solution and ethyl acetate to give 3-(4'-chloro-4-biphenylyl)-butylamine. Hydrochloride, m.p. 256°–259°.

EXAMPLE 63

(a) 1-Ethylamino-3-(4°-chloro-4-biphenylyl)-butane is obtained, analogously to Example 1, from 1-acetamido-3-(4'-chloro-4-biphenylyl)-butane and LiAlH₄.

(b) 1-Ethylamino-3-(4'-chloro-4-biphenylyl)-butane is acetaylated, analogously to Example 26, to give 1-(N-ethylacetamido)-3-(4'-chloro-4-biphenylyl)-butane.

(c) 1-(N-Ethyl-acetamido)-3-(4'-chloro-4-biphenylyl)-butane is reduced, analogously to Example 1, employing LiAlH₄ to give 1-diethylamino-3-(4'-chloro-4-biphenyl)-butane, m.p. 42° – 44°.

EXAMPLE 64

A mixture of 2.82 g of 1-acetamido-3-p-biphenylyl-butan-3-ol, 0.1 g of p-toluenesulfonic acid and 70 ml of toluene is boiled for 2 hours under a water separator, 1-Acetamido-3-p-biphenylyl-2-butene is obtained after working up in the customary manner.

The following are obtained analogously by dehydrating the corresponding alcohols:
1-Acetamido-3-(2'-fluoro-4-biphenylyl)-2-butene,
1-acetamido-3-(4'-fluoro-4-biphenylyl)-2-butene, m.p. 174–176°,
1-acetamido-3-(2'-chloro-4-biphenylyl)-2-butene,
1-acetamido-3-(4'-chloro-4-biphenylyl)-2-butene,
1-acetamido-3-(2'-bromo-4-biphenylyl)-2-butene,
1-acetamido-3-(4'-bromo-4-biphenylyl)-2-butene,
1-acetamido-3-(2',4'-difluoro-4-biphenylyl)-2-butene,
1-acetamido-3-(2',4'-dichloro-4-diphenylyl)-2-butene,
1-acetamido-3-(2',4'-dibromo-4-biphenylyl)-2-butene,
1-acetamido-3-p-phenoxy-phenyl-2-butene,
1-acetamido-3-(4-o-fluorophenoxy-phenyl)-2-butene,
1-acetamido-3-(4-p-fluorophenoxy-phenyl)-2-butene,
1-acetamido-3-(4-o-chlorophenoxy-phenyl)-2-butene,
1-acetamido-3-(4-p-chlorophenoxy-phenyl)-2-butene,
1-acetamido-3-(4-o-bromophenoxy-phenyl)-2-butene,
1-acetamido-3-(4-p-bromophenoxy-phenyl)-2-butene,
1-acetamido-3-[4-(2,4-difluorophenoxy)-phenyl]-2-butene,
1-acetamido-3-[4-(2,4-dichlorophenoxy)-phenyl]-2-butene and
1-acetamido-3-[4-(2,4-dibromophenoxy)-phenyl]-2-butene.

EXAMPLE 65

2.25 g of 3-p-biphenylyl-butylamine are dissolved in 30 ml of formic acid, 10 ml of acetic anhydride are added dropwise at 60°, while stirring, and the mixture is allowed to stand overnight and worked up in the customary manner to give 1-formamido-3-p-biphenylyl-butane.

The examples which follow relate to pharmaceutical preparations which contain amines of Formula I or their acid addition salt.

EXAMPLE A: Tablets

A mixture of 1 kg of 3-(4'-chloro-4-biphenylyl)-butylamine tartrate, 4 kg of lactose, 1.2 kg of potato starch, 0.2 kg of talc and 0.1 kg of magnesium stearate is pressed into tablets in the customary manner, in such a way that each tablet contains 100 mg of active compound.

EXAMPLE B: Dragees

Tablets are pressed analogously to Example A, and are then coated in the customary manner with a coating of sucrose, potato starch, talc, tragacanth and colorant.

EXAMPLE C: Capsules 5 kg of 3-(4'-fluoro-4-biphenylyl)-butylamine hydrochloride are filled into hard gelatine capsules in the customary manner, in such a way that each capsule contains 250 mg of the active compound.

Tablets, dragees and capsules which contain one or more of the remaining active compounds of Formula I and/or their physiologically acceptable acid addition salts, can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An araliphatic nitrogen compound of the formula

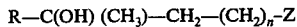

wherein R is 4-biphenylyl monosubstituted or polysubstituted by F, Cl and/or Br; Z is $-NR^1R^2$, $R^1$ and $R^2$ each are H or alkyl of 1–6 carbon atoms, or, collectively, are alkylene of 4–7 carbon atoms; and $n$ is 0, 1 or 2, and their physiologically acceptable acid addition salts.

2. A compound of claim 1 wherein Z is piperidino.
3. A compound of claim 1 wherein A is -C(OH)(CH$_3$)CH$_2$CH$_2$.
4. A compound of claim 1 wherein Z is amino.
5. A compound of claim 1 wherein Z is pyrrolidino.
6. A compound of claim 1 wherein Z is dialkylamino.
7. A compound of claim 1 wherein Z is monoalkylamino.
8. A compound of claim 1, 1-piperidino-3-(4'-fluoro-4-biphenylyl)-butan-3-ol or a physiologically acceptable acid addition salt thereof.
9. A compound of claim 1, 3-(2'-fluoro-4-biphenylyl)-3-hydroxy-butylamine or a physiologically acceptable salt thereof.
10. A compound of claim 1, 3-(4'-fluoro-4-biphenylyl)-3-hydroxy-butylamine or a physiologically acceptable salt thereof.
11. A compound of claim 1, 3-(4'-chloro-4-biphenylyl)-3-hydroxy-butylamine or a physiologically acceptable salt thereof.
12. A compound of claim 1, 3-(2',4'-difluoro-4-biphenylyl)-3-hydroxy-butylamine or a physiologically acceptable salt thereof.
13. A compound of claim 1, 1-piperidino-3-(4'-bromo-4-biphenylyl)-butan-3-ol or a physiologically acceptable salt thereof.
14. A pharmaceutical composition comprising in unit dosage form, an anti-inflammatorily effective amount per unit dosage of a compound of claim 1 in admixture with a pharmaceutically acceptable carrier.
15. A method of treating inflammatory conditions which comprises administering systemically to the affected patient an anti-inflammatorily effective amount of a compound of claim 1.
16. 3-p-Biphenylyl-3-hydroxy-butylamine or a physiologically acceptable salt thereof.
17. 1-Piperidino-3-p-biphenylyl-butan-3-ol or a physiologically acceptable salt thereof.

UNITED STATES PATENT AND TRADEMARK OFFICE
CERTIFICATE OF CORRECTION

PATENT NO. : 4,110,447
DATED : August 29, 1978
INVENTOR(S) : JOACHIM GANTE ET AL It is certified that error appears in the above—identified patent and that said Letters Patent are hereby corrected as shown below:

Title: reads "ANTI-INFLAMMATORY (HOLO-4-BIPHENYLYL) - ALKANOLAMINES"

should read -- ANTI-INFLAMMATORY (HALO-4-BIPHENYLYL) - ALKANOLAMINES --

Signed and Sealed this

Twenty-seventh Day of March 1979

[SEAL]

Attest:

RUTH C. MASON
Attesting Officer

DONALD W. BANNER
Commissioner of Patents and Trademarks